US007556960B2

United States Patent

(12) United States Patent
Hilton et al.

(10) Patent No.: US 7,556,960 B2
(45) **Date of Patent: *Jul. 7, 2009**

(54) PSEUDOMYCIN PRODUCTION BY PSEUDOMONAS SYRINGAE

(75) Inventors: Matthew Dale Hilton, Indianapolis, IN (US); Robert Joseph Strobel, Jr., Carmel, IN (US); Penelope Jane Beverly Millar, Indianapolis, IN (US); Dennis Nelson Thomas, Fairland, IN (US); Andrew Richard Cockshott, Indianapolis, IN (US); Brian Gerald Getman, Greenwood, IN (US); Jack Richard Eastridge, Indianapolis, IN (US); Cathleen Alice Cantwell, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/127,447

(22) Filed: May 12, 2005

(65) Prior Publication Data

US 2006/0257973 A1 Nov. 16, 2006

Related U.S. Application Data

(62) Division of application No. 09/958,996, filed as application No. PCT/US00/08728 on Apr. 14, 2000, now Pat. No. 6,919,188.

(60) Provisional application No. 60/129,431, filed on Apr. 15, 1999.

(51) Int. Cl.
*A01N 63/00* (2006.01)
*C12N 1/20* (2006.01)

(52) U.S. Cl. .................. 435/253.3; 424/93.47; 435/874

(58) Field of Classification Search ....................... None
See application file for complete search history.

(56) References Cited

U.S. PATENT DOCUMENTS

| | | | | |
|---|---|---|---|---|
| 5,576,298 A | 11/1996 | Strobel et al. | ................. | 514/15 |
| 5,981,264 A | 11/1999 | Strobel et al. | | |
| 6,630,147 B1 | 10/2003 | Kulanthaivel et al. | | |
| 7,326,689 B2 * | 2/2008 | Strobel et al. | ................. | 514/15 |

FOREIGN PATENT DOCUMENTS

| | | |
|---|---|---|
| EP | 0272669 | 6/1988 |
| WO | WO-0063237 | 10/2000 |

OTHER PUBLICATIONS

Oka et al. (1981). "Nucleotide Sequence of the Kanamycin Resistance Transposon Tn 903," J. Mol. Biol., 147:217-226.

Gross, D.C. et al. (Feb. 1985). "Regulation of Syringomycin Synthesis in *Pseudomonas syringae* pv. *syringae* and Defined Conditions for Its Production," Journal of Applied Bacteriology. 58(2):167-174.

Lam et al. (1987). "Transposon Mutagenesis and Tagging of Fluorescent Pseudomonas; and Antimycotic Production is Necessary for Control of Dutch Elm Disease," Proc. Natl. Acad. Sci., USA, 84:6447-6451.

Surico, G. et al. (1988). "Production of Syringomycin and Syringotoxin in Culture of *Pseudomonas syringae* pv. *syringae*," Phytopath. Medit., 27(3):163-168.

Harrison, L. et al. (Dec. 1991). "Pseudomycins, a Family of Novel Peptides from *Pseudomonas syringae* Possessing Broad-Spectrum Antifungal Activity." Journal of General Microbiology, 137(12):2857-2865.

Palmer D.A. et al. (May 1993). "Effects of Environmental and Nutritional Factors on Production of the Polyketide Phytotoxin Coronatine by *Pseudomonas syringae* pv. *Glycinea*," Applied and Environmental Microbiology, 59(5):1619-1626.

Ballio. A. et al. (Nov. 21, 1994). "Novel Bioactive Lipodepsipeptides from*Pseudomonas syringae*: the Pseudomycins," FEBS Letters, 355(1):96-100.

Coiro, V.M. et al. (1998). "Solution Conformation of the *Pseudomonas syringae* MSU 16H Phytotoxic Lipodepsipeptide Pseudomycin A Determined by Computer Simulations Using Distance Geometry and Molecular Dynamics from NMR Date," Eur. J. Biochem. 257(2):449-456.

* cited by examiner

*Primary Examiner*—David M. Naff
*Assistant Examiner*—Deborah K. Ware
(74) *Attorney, Agent, or Firm*—Woodard, Emhardt, Moriarty, McNett & Henry LLP

(57) ABSTRACT

A method for producing one or more pseudomycins is described including cultures of *Pseudomonas syringae* that produce one or more pseudomycins having general formula (I) where R is a lipophilic moiety.

(I)

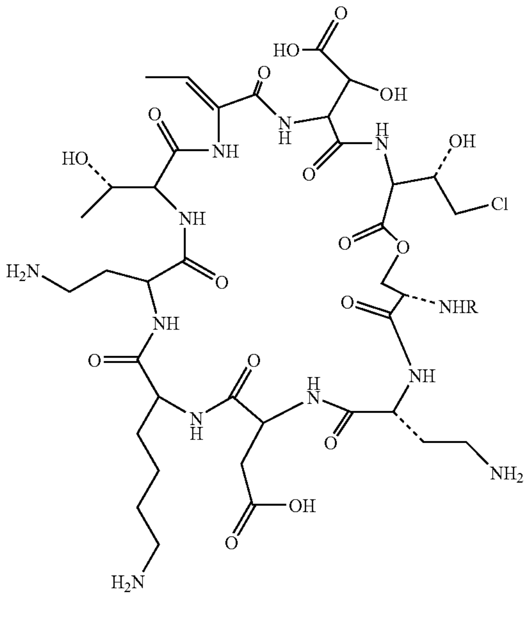

16 Claims, 9 Drawing Sheets

PSEUDOMYCIN PRODUCTION BY PSEUDOMONAS SYRINGAE

FIELD OF THE INVENTION

The present invention relates to a method for producing one or more pseudomycins and to cultures of *Pseudomonas syringae* that produce one or more pseudomycins.

BACKGROUND

Fungal infections are a significant cause of disease, degradation of quality of life, and mortality among humans, particularly for immune compromised patients. The incidence of fungal infections in humans has increased greatly in the past 20 years. This is in part due to increased numbers of people with immune systems weakened or devastated by organ transplants, cancer chemotherapy, AIDS, age, and other similar disorders or conditions. Such patients are prone to attack by fungal pathogens that are prevalent throughout the population but are kept in check by a functioning immune system. These pathogens are difficult to control because some existing antifungal agents are either highly toxic or only inhibit fungal activity. For example, the polyenes are fungicidal but toxic; whereas, the azoles are much less toxic but only fungistatic. More importantly, there have been recent reports of azole and polyene resistant strains of *Candida* which severely limits therapy options against such strains.

One class of new antifungal agents, the pseudomycins, shows great promise for treating fungal infections in a variety of patients. (see i.e., Harrison, L., et al., "Pseudomycins, a family of novel peptides from *Pseudomonas syringae* possessing broad-spectrum antifungal activity," *J. Gen. Microbiology,* 137(12), 2857-65 (1991) and U.S. Pat. Nos. 5,576,298 and 5,837,685). Pseudomycins are natural products derived from isolates of *Pseudomonas syringae. P. syringae* is a large group of plant-associated bacteria that have been the source of several bioactive substances, such as bacitracin and the syringomycins. Natural strains and transposon-generated mutants of *P. syringae* produce compounds with antifungal activity. A transposon-generated regulatory mutant of the wild type strain of *P. syringae* MSU 174, known as MSU 16H (ATCC 67028), produces several pseudomycins. Pseudomycins A, B, C and C' have been isolated, chemically characterized, and shown to possess wide spectrum antifungal activity, including activity against important fungal pathogens in both humans and plants. The pseudomycins are structurally related to but are distinct from syringomycin and other antimycotics from isolates of *P. syringae*. The peptide moiety for pseudomycins A, B, C, C' corresponds to L-Ser-D-Dab-L-Asp-L-Lys-L-Dab-L-aThr-Z-Dhb-L-Asp(3-OH)-L-Thr(4-Cl) with the terminal carboxyl group closing a macrocyclic ring on the OH group of the N-terminal Ser. The analogs are distinguished by the N-acyl side chain, i.e., pseudomycin A is N-acylated by 3,4-dihydroxytetradeconoate, pseudomycin B by 3-hydroxytetradecanoate, pseudomycin C by 3,4-dihydroxyhexadecanoate and pseudomycin C' by 3-hydroxyhexadecanoate. (see i.e., Ballio, A., et al., "Novel bioactive lipodepsipeptides from *Pseudomonas syringae*: the pseudomycins," *FEBS Letters,* 355(1), 96-100, (1994) and Coiro, V. M., et al., "Solution conformation of the *Pseudomonas syringae* MSU 16H phytotoxic lipodepsipeptide Pseudomycin A determined by computer simulations using distance geometry and molecular dynamics from NMR data," *Eur. J. Biochem.,* 257(2), 449-456 (1998).)

Despite the increase in prevalence of fungal infections and the promise of pseudomycins, production of commercial-scale quantity pseudomycins has proved problematic. Published methods for producing pseudomycins are conducted in culture without agitation or stirring and employing expensive potato dextrose medium. Such cultures typically produce pseudomycins in small amounts suitable for laboratory studies and concentrations that are unsuitable for production on a large or commercial scale. Still culture is also unsuitable for use on a scale of greater than about one liter where diffusion of nutrients, gases, especially oxygen, and maintaining adequate cell growth become problematic.

There remains a need for a method for producing pseudomycins using *P. syringae* on a scale and at a concentration suitable for commercial uses of the pseudomycins as antifungal agents for application against infections in animals, humans, or plants.

SUMMARY OF THE INVENTION

The invention provides using microorganisms in a method for producing an antifungal agent, such as one or more pseudomycins. The method involves culturing *Pseudomonas syringae* in media including three or fewer amino acids and recovering one or more pseudomycins from the culture. The three or fewer amino acids include glutamic acid, glycine, histidine, or a combination thereof. In one embodiment, *P. syringae* culture is in medium including glycine and, optionally, a lipid, a potato product, or a combination thereof at a pH of about 4 to 6.5 until one or more pseudomycins is produced at a concentration of at least about 10 μg/mL, preferably more than about 40 μg/mL. The method is especially useful to produce one or more pseudomycins on a scale sufficient for recovering one or more pseudomycins for use as an antifungal agent for treating animals, humans or plants. In addition, pseudomycins prepared by the method described above is also provided.

This invention also relates to biologically-purified cultures of the *P. syringae* strains that are useful for producing pseudomycins. Strains of *P. syringae* can be wild type strains isolated from environmental sources including plants, such as barley plants, citrus plants, lilac plants, and the like; strains selected from such environmental isolates; and mutants of such strains. Preferred environmental isolates are from plants. Preferred *P. syringae* have characteristics including ability to grow and produce one or more pseudomycins on medium lacking potato products or on minimal medium; to produce pseudomycins at significant levels, such as at least about 10 μg/mL; to produce a desired distribution of pseudomycins; and/or to inhibit growth of one or more fungi.

According to the invention, the *P. syringae* exhibits sustained growth and metabolism in a nutrient medium including three or fewer amino acids and, optionally, a lipid, a potato product, or a combination thereof until one or more pseudomycins is produced at a concentration of at least about 10 μg/mL. More preferably, the *P. syringae* strain produces about 40 μg/mL to about 700 μg/mL of one or more pseudomycins, and most preferably about 200 μg/mL of pseudomycin A or at least about 100 μg/mL of pseudomycin B.

In a preferred embodiment of the method, one or more pseudomycins are produced by growth of a strain of *P. syringae* under fed-batch or continuous culture conditions. The *P. syringae* cultures grow for sufficient time and at sufficient density to enhance pseudomycin production. Preferably, the culture is maintained at pH from about 4 to about 6.5 more preferably at a pH from 4.5 to 5.5 to maintain the stability of the pseudomycin.

DEFINITIONS

As used herein, the term "pseudomycin" refers to compounds having the following formula I:

I

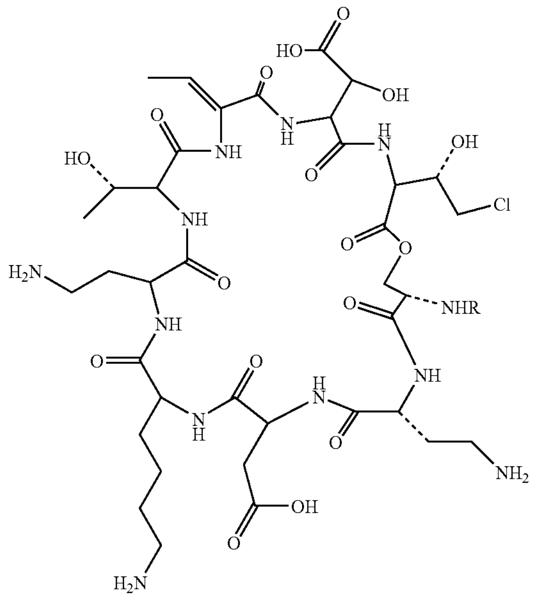

where R is a lipophilic moiety. The pseudomycin compounds A, A', B, B', C, C' are represented by the formula I above where R is as defined below.

Pseudomycin A R=3,4-dihydroxytetradecanoyl
Pseudomycin A' R=3,4-dihydroxypentadecanoate,
Pseudomycin B R=3-hydroxytetradecanoyl
Pseudomycin B' R=3-hydroxydodecanoate
Pseudomycin C R=3,4-dihydroxyhexadecanoyl
Pseudomycin C' R=3-hydroxyhexadecanoyl

DETAILED DESCRIPTION

*Pseudomonas syringae*

Figure 1:
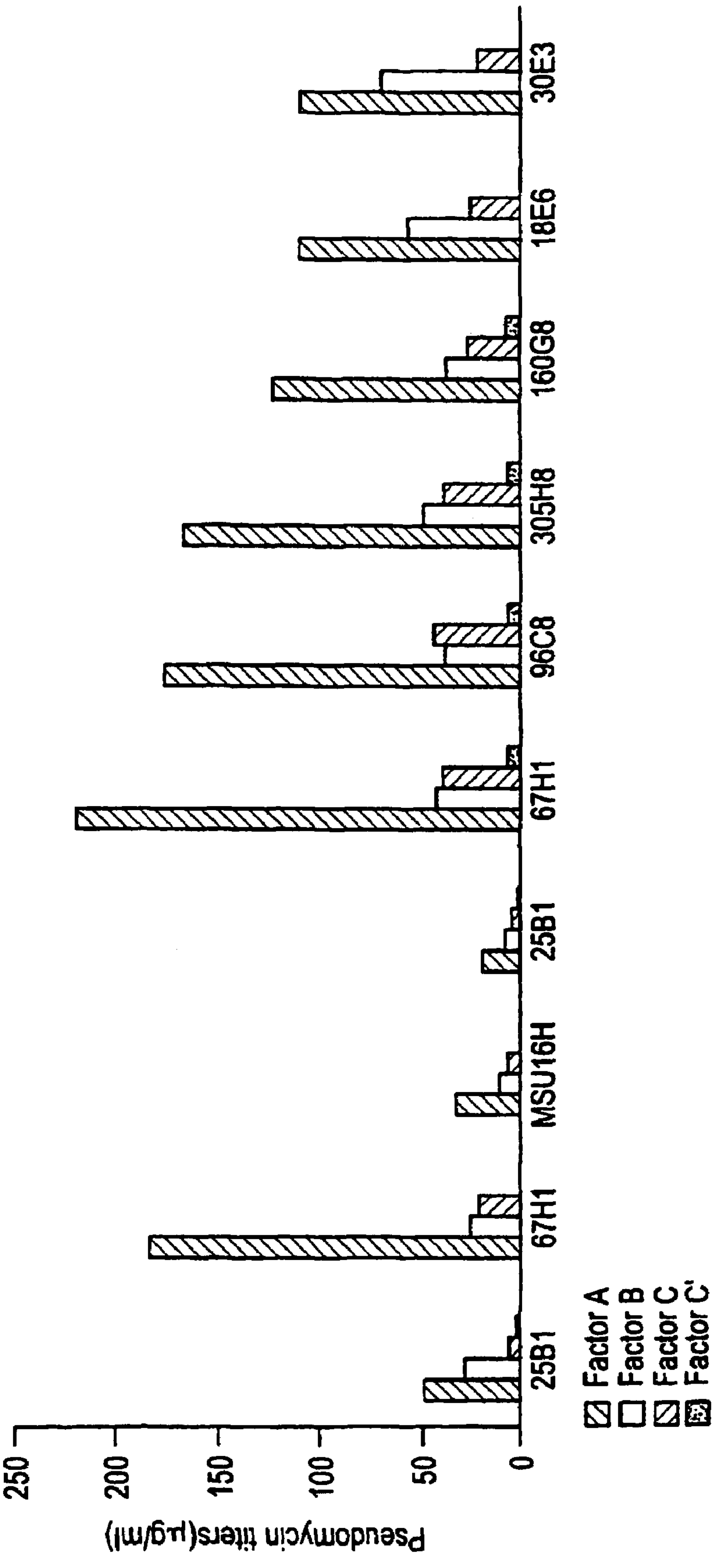
FIG. 1 illustrates levels of production of pseudomycins A, B, C, and C' by several strains of *P. syringae* cultured in N21SM or potato pearl medium for ~67 hours.

*Pseudomonas syringae* include a wide range of bacteria that are generally associated with plants. Some of the *P. syringae* are plant pathogens, while others are only weakly pathogenic or are saprophytes. Many different isolates of *P. syringae* produce one or more cytotoxic agents that can help this bacterium survive in the wild where it must compete with fungi and other bacteria. The cytotoxic agents produced by *P. syringae* include antifungal agents such as the pseudomycins, the syringomycins, the syringotoxins, and the syringostatins.

Isolated strains of *P. syringae* that produce one or more pseudomycins are known in the art. For example, wild type strain MSU 174 (isolated from a Montana barley field) and a mutant of this strain generated by transposon mutagenesis using Tn905 (MSU 16H), have been described in U.S. Pat. No. 5,576,298, issued Nov. 19, 1996 to G. Strobel et al.; Harrison et al., "Pseudomycins, a family of novel peptides from *Pseudomonas syringae* possessing broad-spectrum antifungal activity," *J. Gen. Microbiology* 137, 2857-2865 (1991); Lamb et al., "Transposon mutagenesis and tagging of fluorescent pseudomonas; and Antimycotic production is necessary for control of Dutch elm disease," *Proc. Natl. Acad. Sci. USA* 84, 6447-6451 (1987). Cultures of MSU 174 and MSU 16H are on deposit at Montana State University (Bozeman, Mont., USA) and available from the American Type Culture Collection (Parklawn Drive, Rockville, Md., USA). The disclosures of the references cited in this paragraph are incorporated herein by reference.

The present invention includes a strain, an isolate, and a biologically-purified culture of *P. syringae* that produce one or more pseudomycins in amounts greater than about 10 μg/mL, preferably from at least about 10 μg/mL to about 900 μg/mL, and more preferably from about 800 μg/mL to about 900 μg/mL. Preferably, the biologically-purified culture of a microorganism is of *Pseudomonas syringae* strain MSU 16H, 25-B1, 67H1, 7H9-1, or 7D11-6, or a pseudomycin-producing mutant, variant, isolate, or recombinant of these strains. Cultures MSU 174 and MSU 16H were obtained as described in the references cited herein above.

A strain of *P. syringae* that is suitable for production of one or more pseudomycins can be isolated from environmental sources including plants, such as barley plants, citrus plants, lilac plants, and the like, and also from sources such as soil, water, air, dust, and the like. A preferred strain is isolated from plants. Strains of *P. syringae* that are isolated from environmental sources can be referred to as wild type. As used herein, "wild type" refers to a dominant genotype which naturally occurs in the normal population of *P. syringae* (i.e., strains or isolates of *P. syringae* that are found in nature and not produced by laboratory manipulation). As is the case with other organisms, the characteristics of the pseudomycin-producing cultures employed in this invention, *P. syringae* strains such as MSU 174, MSU 16H, MSU 206, 25-B1, and 7H9-1 are subject to variation. Thus, progeny of these strains, e.g., recombinants, mutants and variants, may be obtained by methods well-known to those skilled in the art.

Mutant strains of *P. syringae* are also suitable for production of one or more pseudomycins. As used herein, "mutant" refers to a sudden heritable change in the phenotype of a strain, which can be spontaneous or induced by known mutagenic agents, including radiation and various chemicals. Mutant *P. syringae* of the present invention can be produced using a variety of mutagenic agents including radiation; such as ultraviolet light, or x-rays; chemical mutagens, site-specific mutagenesis, and transposon mediated mutagenesis. Examples of chemical mutagens are ethyl methanesulfonate (EMS), diepoxyoctane, N-methyl-N-nitro-N'-nitrosoguanine (NTG), and nitrous acid.

Pseudomycin-producing mutants of *P. syringae* of the present invention can be produced by treating the bacteria with an amount of a mutagenic agent effective to produce mutants that overproduce one or more pseudomycins, that produce one pseudomycin, such as pseudomycin B, in excess over other pseudomycins, or that produce one or more pseudomycins under advantageous growth conditions. While the type and amount of mutagenic agent to be used can vary, a preferred method is to serially dilute NTG to levels ranging from 1 to 100 μg/ml. Preferred mutants of the invention are those X that overproduce pseudomycin B and grow in minimal defined media. The mutants overproduce one or more pseudomycins preferably from at least about 10 μg/mL to about 900 μg/mL, and more preferably from about 800 μg/mL to about 900 μg/mL.

Environmental isolates, mutant strains, and other desirable strains of *P. syringae* can be subjected to selection for desirable traits of growth habit, growth medium, nutrient source, carbon source, growth conditions, and amino acid requirements. Preferably, a pseudomycin producing strain of *P. syringae* is selected for growth on minimal defined medium, such as N21 medium, and/or for production of one or more pseudomycins at levels greater than about 10 μg/mL. Preferred strains exhibit the characteristic of producing one or more pseudomycins when grown on a medium including three or fewer amino acids and, optionally, either a lipid, a potato product, or a combination thereof.

Recombinant strains can be developed by transforming the *P. syringae* strains, using procedures well-known to those skilled in the art. Through the use of recombinant DNA technology, the *P. syringae* strains can be transformed to express a variety of gene products in addition to the antibiotics these strains produce. For instance, one can transform the strains with a recombinant vector that confers resistance to an antibiotic to which the strains are normally sensitive. Transformants thus obtained will produce not only pseudomycins but also the resistance-conferring enzyme that allows selection of the transformed from wild-type cells. Furthermore, using similar techniques, one can modify the present strains to introduce multiple copies of the endogenous pseudomycin biosynthesis genes to achieve greater pseudomycin yield. Progeny, i.e. natural and induced variants, mutants and recombinants, of the *P. syringae* strains 25-B1, 67H1, and 7H9-1 which retain the characteristic of pseudomycin overproduction are part of this invention.

Pseudomycins

As used herein, pseudomycin refers to one or more members of a family of antifungal agents that has been isolated from the bacterium *Pseudomonas syringae*. A pseudomycin is a lipodepsipeptide, a cyclic peptide including one or more unusual amino acids and having one or more appended hydrophobic or fatty acid side chains. Specifically, the pseudomycins are lipodepsinonapeptides, with a cyclic peptide portion closed by a lactone bond and including the unusual amino acids 4-chlorothreonine, 3-hydroxyaspartic acid, dehydro-2-aminobutyric acid, and 2,4-diaminobutyric acid. It is believed that these unusual amino acids are involved in biological characteristics of the pseudomycins, such as stability in serum and their killing action. Pseudomycins include pseudomycin A, pseudomycin A', pseudomycin B, pseudomycin B', pseudomycin C, and pseudomycin C'. Each of these pseudomycins has the same cyclic peptide nucleus, but they differ in the hydrophobic side chain attached to this nucleus.

Pseudomycins A, A', B, B', C and C' have each been isolated and purified and their structures have been characterized by methods including amino acid sequencing, NMR, and mass spectrometry. Pseudomycins A, B, C, and C' are discussed in U.S. Pat. No. 5,576,298, issued Nov. 19, 1996 to G. Strobel et al.; Harrison et al., "Pseudomycins, a family of novel peptides from *Pseudomonas syringae* possessing broad-spectrum antifungal activity," *J. Gen. Microbiology* 137, 2857-2865 (1991); and Ballio et al., "Novel bioactive lipodepsipeptides from *Pseudomonas syringae*: the pseudomycins," *FEBS Lett.* 355, 96-100 (1994). Pseudomycins A' and B' are described in U.S. patent application Serial No. PCT/US00/08727, by Palaniappan Kulanthaivel, et al. entitled "Pseudomycin Natural Products" submitted evendate herewith and exemplified in the Examples. Antifungal activity due to several pseudomycins was traced to *P. syringae* bearing a transposon known as Tn 903, which encodes factors including kanamycin resistance. The sequence of and methods for manipulating transposon Tn 903 are known. Oka et al., "Nucleotide sequence of the kanamycin resistance transposon Tn 903," *J. Mol. Biol.* 147, 217-226 (1981). Each of the references cited in this paragraph is specifically incorporated herein by reference.

The pseudomycins vary in structure and properties. Preferred pseudomycins A, B, C and C' exhibit activity against a wide variety of fungi and also exhibit generally acceptable toxicity. Compared to the other preferred pseudomycins, pseudomycin B has greater potency against certain fungi and a lower level of toxicity. Therefore, for the present methods, pseudomycin B is more preferred. Each pseudomycin has a cyclic nonapeptide ring having the sequence Ser-Dab-Asp-Lys-Dab-aThr-Dhb-HOAsp-ClThr (Serine; 2,4-Diaminobutyric acid; Aspartic acid; Lysine; 2,4-Diaminobutyric acid; alloThreonine; Dehydro-2-aminobutyric acid; 3-hydroxyAspartic acid; 4-chloroTheonine), more specifically, L-Ser-D-Dab-L-Asp-L-Lys-L-Dab-L-aThr-Z-Dhb-L-Asp(3-OH)-L-Thr(4-Cl), with the carboxyl group of the ClThr and the hydroxyl group of the serine closing the ring with a lactone bond. The pseudomycins differ in the nature of the lipophilic moiety that is attached to the amine group of the N-terminal serine. The amine group of the serine forms an amide bond with the carboxyl of a 3,4-dihydroxytetradecanoyl moiety in pseudomycin A, a 3-monohydroxytetradecanoyl moiety in pseudomycin B, a 3,4-dihydroxyhexadecanoyl moiety in pseudomycin C and a 3-monohydroxyhexadecanoyl moiety in pseudomycin C'. The carboxyl group of the serine forms an amide bond with the Dab of the ring.

Biological Activities of Pseudomycins

A pseudomycin has several biological activities including killing various fungi, such as fungal pathogens of plants and animals. In particular, a pseudomycin is an active antimycotic agent against fungi that cause opportunistic infections in immune compromised individuals. These fungi include various species of *Candida* including *C. parapsilosis, C. albicans, C. glabrata, C. tropicalis*, and *C. krusei*. They also include other genera such as *Cryptococcus neoformans, Aspergillus fumigatus*, and *Histoplasma capsulatum*. Killing, rather than inhibiting the growth of fungi, particularly of fungal pathogens, is a desirable and preferred biological activity of a pseudomycin.

The pseudomycins have been also shown to be toxic to a broad range of plant-pathogenic fungi including *Rynchosporium secalis, Ceratocystis ulmi, Rhizoctonia solani, Sclerotinia sclerotiorum, Verticillium albo-atrum, Verticillium dahliae, Thielaviopis basicola, Fusarium oxysporum* and *Fusarium culmorum*. (see Harrison, L., et al., "Pseudomycins, a family of novel peptides from *Pseudomonas syringae* possessing broad-spectrum antifungal activity," *J. of General Microbiology,* 7, 2857-2865 (1991).) In addition, *P. syringae* MSU 16H has been shown to confer a greater protection than the wild-type strain in elms infected with *Ceratocystic ulmi*, the causal agent of Dutch elm disease. (see e.g., Lam et al, *Proc. Natl. Sci. USA,* 84, 6447-6451 (1987)).

Growth of *Pseudomonas syringae*

As described herein, "aqueous nutrient media" refers to a water-base composition including minerals and organic compounds and their salts necessary for growth of the microorganism used in the present invention. Preferred nutrient media contain an effective amount of three or fewer amino acids, preferably, glutamic acid, glycine, histidine, or a combination thereof. In one embodiment, the medium contains an effective amount of glycine and, optionally, one or more of a potato product and a lipid. Glycine can be provided as a single amino acid or as part of a mixture of amino acids, such as hydrolyzed protein. Suitable lipids include soybean oil, fatty acids with a 14 or 16 carbon aliphatic chain, and fatty acid esters with a 14 or 16 carbon aliphatic chain. Preferred fatty acid esters include methyl palmitate and methyl myristate, preferably methyl myristate. Suitable potato products include potato dextrose broth, potato dextrin, potato protein, and commercial mashed potato mix food product. Preferred minerals in the nutrient medium include salt mixtures typically used in cell culture and fermentation, such as Czapek mineral salts, which includes KCl, $MgSO_4$, and $FeSO_4$. Organic compounds in the nutrient media preferably include glucose or sucrose and can optionally include soluble starch; other like organic compounds can also be included. The pH of the medium is preferably from about 4 to 6.5, more preferably from about 4.5 to about 5.7, most preferably about 5.2.

Although the amount of each ingredient in the nutrient broth is not typically critical to growth of the bacteria or to production of one or more pseudomycins, certain levels of nutrients are advantageous. A preferred amount of glycine is about 0.1 g/L to about 10 g/L, more preferably about 0.3 g/L to about 3 g/L, most preferably about 1 g/L. A preferred amount of lipid is about 1 g/L to about 10 g/L of an oil product such as soybean oil, more preferably about 0.5 g/L to about 2 g/L of soybean oil. A preferred amount of a fatty acid or fatty acid ester is about 0.5 g/L to about 5 g/L. A preferred fatty acid ester is methyl myristate, in amounts of about 0.1 to about 10 g/L, preferably about 0.3 g/L to about 3 g/L more preferably about 1 g/L. Preferred amounts of potato products include about 12 g/L to about 36 g/L, more preferably about 24 g/L of potato dextrose broth; about 5 g/L to about 50 g/L, more preferably about 30 g/L of commercial mashed potato mix; about 1 g/L to about 30 g/L, preferably about 20 g/L of potato dextrin; and/or about 1 g/L to about 10 g/L, preferably about 4 g/L of potato protein. A preferred nutrient medium includes minerals, such as, KCl at about 0.02 to about 2 g/L, more preferably about 0.2 g/L; $MgSO_4$, preferably $MgSO_4.7H_2O$, at about 0.02 to about 2 g/L, more preferably about 0.2 g/L; $FeSO_4$, preferably $FeSO_4.7H_2O$, at about 0.4 to about 40 mg/L, more preferably about 4 mg/L; and the like. When present, soluble starch is preferably at about 0.5 to about 50 g/L, more preferably about 5 g/L. Glucose is preferably present at about 2 to about 80 g/L, more preferably about 20 g/L. Sucrose is preferably present at about 2 to about 80 g/L, more preferably about 30 g/L

*P. syringae* is typically grown in the media described under conditions of controlled or regulated pH, temperature, and the like *P. syringae* grow and produce one or more pseudomycins at temperatures between about 15° C. and about 35° C., preferably about 20° C. to about 30° C., more preferably about 22° C. to about 27° C., most preferably about 25° C. *P. syringae* grow and produce one or more pseudomycins at pH between about 4 and about 7, preferably about 4 and about 6, more preferably about 4.5 to about 5.5. Typically growth of *P. syringae* does not occur when the temperature is above 37° C. or below 10° C. or when the pH is above 9 or below 4.

Method for Pseudomycin Production

To produce one or more pseudomycins from a wild type or mutant strain of *P. syringae*, the organism is cultured with agitation in an aqueous nutrient medium including an effective amount of three or fewer amino acids. The three or fewer amino acids are preferably glutamic acid, glycine, histidine, or a combination thereof. In one preferred embodiment, the amino acids include glycine and, optionally, one or more of a potato product and a lipid. Culturing is conducted under conditions effective for growth of *P. syringae* and production of the desired pseudomycin or pseudomycins. Effective conditions include temperature of about 22° C. to about 27° C., and a duration of about 36 hours to about 96 hours. When cultivated on the media such as those described herein, *P. syringae* can grow in cell densities up to about 10-15 g/L dry weight and produce pseudomycins in total amounts at least about 10 μg/mL, preferably at least about 40 μg/mL more preferably about 500 μg/mL or more.

Controlling the concentration of oxygen in the medium during culturing of *P. syringae* is advantageous for production of a pseudomycin. Preferably, oxygen levels are maintained at about 5% to about 50% saturation, more preferably about 30% saturation. Sparging with air, with pure oxygen, or with gas mixtures including oxygen can regulate the concentration of oxygen in the medium. Further, adjustment of the agitation rate can be used to adjust the oxygen transfer rate.

Controlling the pH of the medium during culturing of *P. syringae* is advantageous for production of a pseudomycin. Pseudomycins are labile at basic pH, and significant degradation can occur if the pH of the culture medium is above about 6 for more than about 12 hours. Preferably, the pH of the culture medium is maintained at less than about 6, more preferably less than about 5.5, and most preferably above 4.0. The pH is preferably maintained at about 5 to about 5.4, more preferably about 5.0 to about 5.2. Although not limiting to the present invention, it is believed that pseudomycin degradation at basic pH is due to opening of the lactone ring and leaving of $Cl^-$.

*P. syringae* can produce one or more pseudomycins when grown in batch culture. However, fed-batch or semi-continuous feed of glucose and, optionally, an acid or base, such as ammonium hydroxide, to control pH, enhances pseudomycin production. Pseudomycin production by *P. syringae* can be further enhanced by using continuous feed methods in which glucose and, optionally, an acid or base, such as ammonium hydroxide, to control pH, are fed automatically.

Employing *P. syringae*, one or more pseudomycins can be produced in substantial quantities. That is, total quantities of one or more pseudomycins from at least about 200 μg/mL to about 900 μg/mL, preferably of from about 600 μg/mL to about 900 μg/mL, more preferably from about 800 μg/mL to about 900 μg/mL. Preferably, for production of pseudomycin A, pseudomycin A is produced in total quantities from at least about 10 μg/mL to about 400 μg/mL, more preferably of from about 300 μg/mL to about 400 μg/mL, most preferably from about 350 μg/mL to about 400 μg/mL. Preferably, for production of pseudomycin B, pseudomycin B is produced in total quantities from at least about 10 μg/mL to about 300 μg/mL, more preferably from about 200 μg/mL to about 300 μg/mL, most preferably from about 250 μg/mL to about 300 μg/mL. Preferably, for production of pseudomycin C, pseudomycin C is produced in total quantities from at least about 5 μg/mL to about 100 μg/mL, more preferably of from about 5 μg/mL to about 50 μg/mL, most preferably from about 10 μg/mL to about 50 μg/mL. Preferably, for production of pseudomycin C', pseudomycin C' is produced in total quantities from at least about 1 μg/mL to about 50 μg/mL, more preferably of from about 10 μg/mL to about 50 μg/mL, most preferably from about 30 μg/mL to about 50 μg/mL.

Choice of *P. syringae* strain can affect the amount and distribution of pseudomycin or pseudomycins produced by culturing under the conditions described herein. For example, strains MSU 16 H and 67 H1, and like strains, each produce predominantly pseudomycin A, but also produce pseudomycin B and C, typically in ratios of roughly 4:2:1. Strain 67 H1 and like strains, however, typically produce levels of pseudomycins about 3- to about 5-fold larger than are produced by strain MSU 16H. Compared to strains MSU 16 H and 67 H1, strain 25-B1 and like strains produce more pseudomycin B and less pseudomycin C. Strain 7H9-1 and like strains are distinctive in producing predominantly pseudomycin B and for producing larger amounts of pseudomycin B than other strains. For example this strain can produce pseudomycin B in at least a 10-fold excess over either pseudomycin A or C.

Each pseudomycin or mixtures of pseudomycins can be detected, determined, isolated, and/or purified by any of a variety of methods known to those of skill in the art. For example, the level of pseudomycin activity in a broth or in an isolated or purified composition can be determined by antifungal action against a fungus such as *Candida*. Numerous methods are known for the preparation and analysis of the pseudomycins. For example, one or more pseudomycins can be isolated and purified by chromatography, such as HPLC.

The pseudomycins produced by the process of the present invention may be isolated as their pharmaceutically acceptable salts. The term "pharmaceutically acceptable salt", as used herein, refers to salts of the compounds described above that are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are mineral acids such as hydrochloric acid, hydrobromic acid, hydroiodic acid, sulfuric acid, and phosphoric acid, and organic acids such as p-toluenesulfonic, methanesulfonic acid, oxalic acid, p-bromophenylsulfonic acid, carbonic acid, succinic acid, citric acid, benzoic acid, and acetic acid. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, napththalene-2-sulfonate, and mandelate. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, and bicarbonates. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, and calcium carbonate. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The present invention may be better understood with reference to the following examples. These examples are intended to be representative of specific embodiments of the invention, and are not intended as limiting the scope of the invention.

EXAMPLES

Biological Materials on Deposit

*P. syringae* MSU 16H is publicly available from the American Type Culture Collection, Parklawn Drive, Rockville, Md., USA as Accession No. ATCC 67028. *P. syringae* strains 25-B1, 7H9-1, and 67 H1 were deposited with the American Type Culture Collection on Mar. 23, 2000 and were assigned the following Accession Nos.:

| | |
|---|---|
| 25-B1 | Accession No. PTA-1622 |
| 7H9-1 | Accession No. PTA-1623 |
| 67 H1 | Accession No. PTA-1621 |

Example 1

Determination and Purification of Pseudomycins

Detection and Quantification of Pseudomycins by Antifungal Activity

The presence or amount of a pseudomycin or mixture of pseudomycins can be determined by measuring the antifungal activity of a preparation. Antifungal activity was determined in vitro by obtaining the minimum inhibitory concentration (MIC) of the preparation using a standard agar dilution test or a disc-diffusion test. A preparation of one or more pseudomycins can be an extract of a cell culture, or a more purified mixture. A typical fungus employed in testing antifungal activity is *C. albicans*. Antifungal activity was considered significant when the test preparation (50 μL) caused 10-12 mm diameter zones of inhibition on *Candida albicans* ×657 seeded agar plates.

Detection and Quantification of Pseudomycins by HPLC

A sample believed to contain one or more pseudomycins was first extracted with either an equal volume of acetonitrile or 1.5 volume of methanol/$H_3PO_4$ (0.1% v/v) and then clarified by filtration or centrifugation. The clarified mixture was chromatographed on a Zorbax 300SB-C8 column (3.5 μm particles, 5.0×0.46 cm, MacMod catalog no. 865973-906) with a flow rate of 2 mL/min and a column temperature of 60° C. The column was eluted with a gradient of mobile phase A (25 mM sodium phosphate, 7.74 g/L octane sulfonic acid, and 10% acetonitrile in water at pH 6.5) and mobile phase B (25 mM sodium phosphate, 7.74 g/L octane sulfonic acid, and 60% acetonitrile in water at pH 6.5). Pseudomycins were separated and quantified employing a gradient over 10 min of 28% to 38% mobile phase B. Typically, pseudomycin A eluted at about 10.2 min (612 sec), pseudomycin B at 10.98 min (659 sec), pseudomycin C at 11.5 min (691 sec), pseudomycin B' at 9.6 min (576 sec), and pseudomycin C' at 12.17 min (730 sec). Pseudomycins were detected by absorbance at 214 nm and quantified by integration of uv peaks. Known standards of each of the pseudomycins provided a standard for identification and quantification.

Purification of Pseudomycins from Stirred Fermentors

Broth from a 150 liter, 1000 liter, or other fermentor was filtered to remove cells. The filtrate was loaded onto a HP-20SS column to capture the pseudomycin factors. Fractions were collected while washing the column with 15 to 30% acetonitrile with 0.1% trifluoroacetic acid. Fractions containing the pseudomycins were loaded onto an Amberchrom CG300-sd column. Factor A was eluted with 22-30% acetonitrile in 0.2% sodium acetate buffer (pH 4.8). Factors B, C, and C' were eluted with 25-35% acetonitrile with 0.2% sodium acetate buffer (pH 4.8). Factor A was 85% pure (UV absorption). Factor A was loaded onto a C18 reverse phase HPLC column and eluted with 30-60% acetonitrile with 0.2% trifluoroacetic acid. Eluted material was greater than 95% pure (UV/NMR).

Example 2

Isolation, Characterization and Mutagenesis of *Pseudomonas syringae*

As a first step toward production of large quantities of pseudomycins, environmental isolates of *P. syringae* were selected and mutants of these isolates were generated. These isolates and mutants were then studied for factors that improved pseudomycin production and culture medium.

Materials and Methods

Strains MSU 174 and MSU 16-H were isolated and characterized as described in U.S. Pat. No. 5,576,298, issued Nov. 19, 1996 to G. Strobel et al.; Hanison et al., "Pseudomycins, a family of novel peptides from *Pseudomonas syringae* possessing broad-spectrum antifungal activity," *J. Gen. Microbiology* 137, 2857-2865 (1991), and Lamb et al., "Transposon mutagenesis and tagging of fluorescent pseudomonas: Antimycotic production is necessary for control of Dutch elm disease," *Proc. Natl. Acad. Sci. USA* 84, 6447-6451 (1987). The disclosures of the references cited in this paragraph are incorporated herein by reference.

Additional strains were derived from such wild type and transposon-generated mutants by chemical mutagenesis. Strains subjected to mutagenesis include MSU 174, MSU 16H and 25-B1. The strain to be mutagenized was grown in a medium containing potato product, then divided into the medium including 0, 1, 2, 4, 16, or 32 μg/mL of the chemical mutagen 1-methyl-3-nitro-1-nitrosoguanidine (NTG or MNNG). These cells were then frozen for future screening and selection.

Mutagenized cells were selected for desirable growth conditions and/or pseudomycin production. Chemically mutagenized cells of *P. syringae*, such as mutagenized strain 25-B1, were thawed and diluted to 6 cells/mL in N21SM medium (Table 1). This medium sometimes contained one or more components for selection, such as varying concentrations of phosphate. A 50 μL volume of mutagenized cells was dispensed into a well of a 96-well round bottom microtiter plate for delivery targeting an average of 0.3 cells/well. Typically, silicone oil was added to each well to minimize evaporation. The plates were incubated with shaking for 6 to 12 days at 25° C.

TABLE 1

The Composition of N21SM Medium

| INGREDIENT | GRAMS PER LITER |
|---|---|
| Glucose | 20 |
| Ammonium Sulfate | 0.5 |
| Monosodium Glutamate or L-Glutamic Acid | 2 |
| L-Histidine | 2 |
| Glycine | 0.5 |
| Soluble Starch | 5 |
| $KH_2PO_4$ | 0.2 |
| Czapek Mineral Salts Solution | 2 mL |
| MES Buffer | 9.8 |
| Adjust pH to 5.0 | |

After this incubation, an aliquot, typically 5 μL, from each well was serially diluted (e.g. 1:56, 1:196, 1:320, 1:686, and/or 1:1715) and evaluated for activity against *Candida albicans* in a liquid microtiter plate bioassay. The plates were incubated at 37° C. overnight and the wells were scored for inhibition of *C. albicans* growth. Strains that resulted in inhibition at extremes of dilution (e.g. 1:320, 1:686, and/or 1:1715) were picked, inoculated into CSM medium (Table 2), and grown for 1 to 3 days at 25° C.

TABLE 2

Complete *Streptomyces* Medium (CSM)

| Component | Concentration (g/L) |
|---|---|
| Glucose | 5 |
| Maltose | 4 |
| Difco Tryptic Soy Broth | 30 |
| Difco Yeast Extract | 3 |
| $MgSO_4 \cdot 7H_2O$ | 2 |
| No pH adjustment | |

The selected strains were preserved and inoculated into fermentation bottles containing 13 mL of N21SM medium and grown for approximately 66 hours at 25° C. An aliquot was removed from this fermentation, extracted for 1 hour with a volume of acetonitrile equal to the volume of the aliquot, centrifuged, and decanted for HPLC analysis of pseudomycins as described in Example 1. Strains producing suitable levels of pseudomycins, typically in excess of 10 μg/mL were reisolated, refermented, and prepared for growth on a larger scale.

The medium and growth conditions were also screened for their effect on yield and distribution of pseudomycins. Several components of the medium were varied simultaneously in a statistically designed series of experiments. These experiments selected for a chemically defined medium lacking a potato product, having defined levels of phosphate, having increased clarity, and producing high levels of growth of *P. syringae*.

Results

Figure 2:
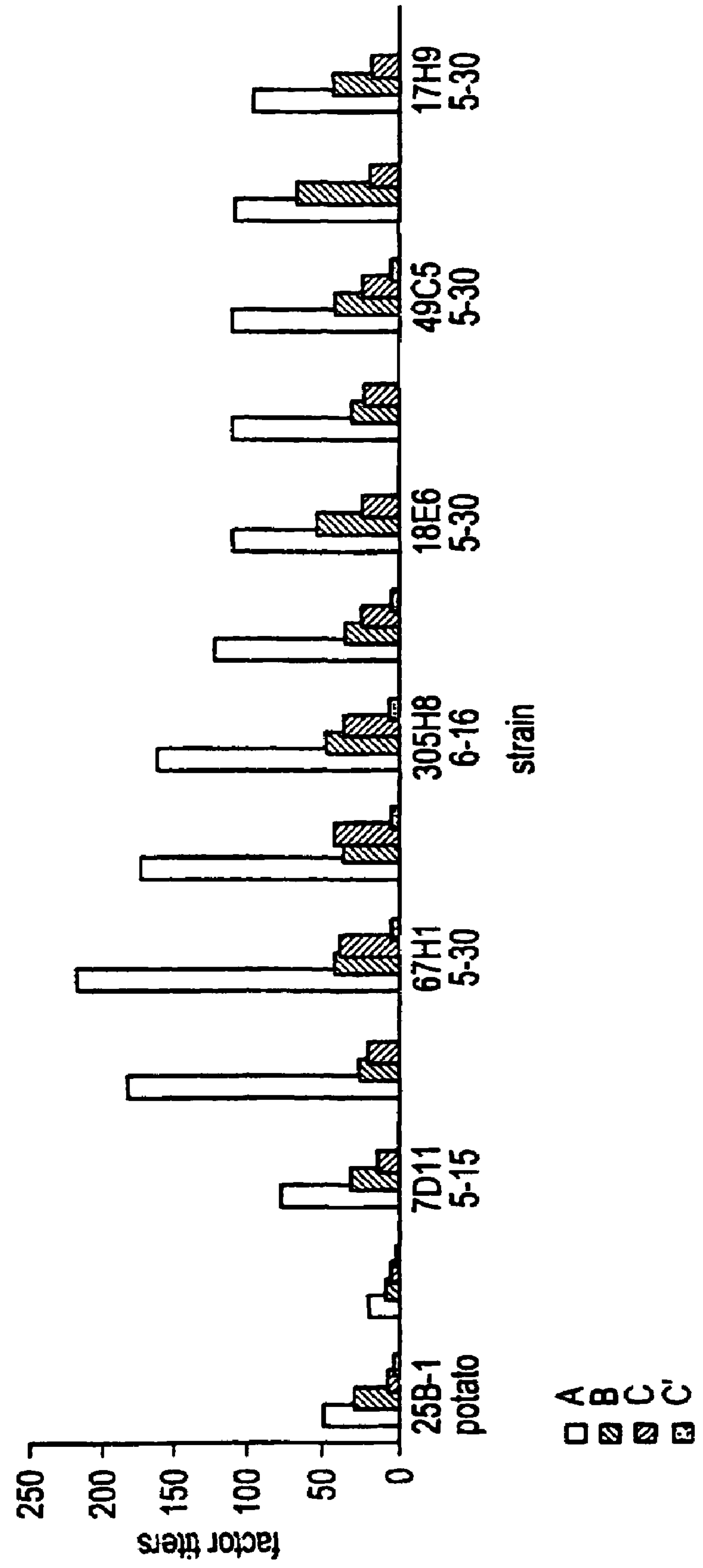
FIG. 2 illustrates levels of production of pseudomycins A, B, C, and C' by several strains of *P. syringae* that have been grown in N21SM in bottles for ~67 hours.

Numerous strains exhibiting high levels of pseudomycin production, producing predominantly a single pseudomycin, and/or growing on minimal medium were produced using the methods described above. Strains producing elevated levels of one or more pseudomycins and a distribution of pseudomycins obtained in a 13 mL fermentation are shown in Table 3. Pseudomycin distributions and levels obtained using a potato medium and N21SM medium are shown for certain mutants in FIGS. 2 and 3.

TABLE 3

Strains Selected for Production of Pseudomycins and/or Growth on Minimal Medium

| | PSEUDOMYCIN (μg/mL) | | | | Cell Density | PSA + PSB/ | PSB/ |
|---|---|---|---|---|---|---|---|
| Strain | A | B | C | C' | ($OD_{600}$) | $OD_{600}$ | PSA |
| 30 E3 | 109 | 69 | | | 0.759 | 234 | 0.64 |
| 40G11 | 81 | 66 | | | 0.818 | 179 | 0.82 |
| 7H9-1 | 3.3 | 60.4 | | | 0.744 | 86 | 18.58 |
| 75F8 | 65 | 57 | | | 0.884 | 137 | 0.88 |
| 18 E6 | 111 | 57 | | | 0.855 | 196 | 0.51 |
| 8 E3 | 38.47 | 55.07 | | | 0.830 | 113 | 1.43 |
| 305H8 | 165.0 | 48 | 39 | 7 | 0.762 | 280 | 0.29 |
| 17H9 | 96 | 46 | | | 0.769 | 185 | 0.48 |
| 67H1-1 | 216.9 | 44.2 | 39.9 | 5.8 | 0.817 | 320 | 0.20 |
| 49C5 | 110 | 43 | | | 0.804 | 190 | 0.39 |
| 67H1 | 197 | 42 | | | 0.817 | 293 | 0.21 |
| 67H1-6 | 225.9 | 42.1 | 40.2 | 4.8 | 0.791 | 339 | 0.19 |
| 67H1-6 | 216.4 | 41.5 | 38.6 | 5 | 0.797 | 324 | 0.19 |
| 67H1-1 | 232.7 | 38.3 | 41.7 | 4.7 | 0.819 | 331 | 0.16 |
| 160G8 | 123.5 | 38 | 27 | 7 | 0.738 | 219 | 0.31 |
| 96C8 | 175.1 | 38 | 44 | 6 | 0.719 | 296 | 0.21 |
| 52G11 | 68 | 36 | | | 0.822 | 127 | 0.53 |
| 11G3 | 110 | 33 | | | 0.675 | 212 | 0.30 |
| 7D11 | 77.13 | 32.73 | | | 0.706 | 156 | 0.42 |
| 8B6 | 72.1 | 32.3 | | | 0.706 | 148 | 0.45 |
| 16E12 | 46.4 | 30 | 10 | 5 | 0.672 | 113 | 0.64 |
| 11B11 | 41 | 29 | | | 0.779 | 89 | 0.71 |
| 49G5 | 61 | 29 | | | 0.744 | 121 | 0.47 |
| 288 E11 | 87.0 | 28 | 20 | 6 | 0.736 | 157 | 0.33 |
| 224H8 | 76.9 | 26 | 20 | 5 | 0.570 | 181 | 0.34 |
| 19D3 | 40 | 24 | | | 0.804 | 80 | 0.60 |
| 37 E9 | 33 | 23 | | | 0.776 | 72 | 0.68 |
| 40B2 | 56 | 23 | | | 0.420 | 187 | 0.40 |
| 13B8 | 38.1 | 21.15 | 9.6 | | 0.676 | 88 | 0.56 |
| 7D10 | 50.95 | 20.4 | 14.05 | | 0.898 | 79 | 0.40 |
| 51D2 | 45 | 20 | | | 0.817 | 80 | 0.45 |
| 49D1 | 41 | 20 | | | 0.826 | 73 | 0.48 |
| 6B7 | 34.35 | 18.3 | 8.55 | | 0.698 | 75 | 0.53 |
| 17G1 | 30 | 17 | | | 0.848 | 55 | 0.58 |
| 159D4 | 30.6 | 15 | 7 | 2 | 0.699 | 65 | 0.50 |
| 1F12 | 47.7 | 14.9 | | | 0.756 | 83 | 0.31 |
| 12E 9 | 64.7 | 14.3 | | | 0.769 | 103 | 0.22 |
| 41G8 | 48 | 14 | | | 0.850 | 73 | 0.30 |
| 37F8 | 43 | 14 | | | 0.935 | 60 | 0.32 |
| 218F10 | 66.0 | 13 | 18 | 1 | 0.619 | 128 | 0.20 |

TABLE 3-continued

Strains Selected for Production of Pseudomycins and/or Growth on Minimal Medium

| | PSEUDOMYCIN (μg/mL) | | | | Cell Density | PSA + PSB/ | PSB/ |
|---|---|---|---|---|---|---|---|
| Strain | A | B | C | C' | ($OD_{600}$) | $OD_{600}$ | PSA |
| 45E10 | 27 | 13 | | | 0.698 | 58 | 0.50 |
| 7G5 | 50.2 | 12.7 | | | 0.703 | 89 | 0.25 |
| 3C11 | 44.4 | 12.5 | | | 0.895 | 64 | 0.28 |
| 18C2 | 29.45 | 12.45 | 7.8 | | 0.474 | 88 | 0.42 |
| 8D6 | 19.43 | 11.63 | | | 0.783 | 40 | 0.60 |
| 6D5 | 2.5 | 11.5 | | | 0.230 | 61 | 4.60 |
| 3C3 | 36.0 | 10.4 | | | 0.622 | 75 | 0.29 |
| 4E 12 | 27.6 | 10.3 | | | 0.695 | 54 | 0.27 |
| 25B-1 | 26.6 | 10.2 | | | | | 0.38 |
| 25B-1 | 26.5 | 10.1 | | | | | 0.38 |
| 40G2 | 26 | 10 | | | 0.489 | 73 | 0.39 |
| 18G1 | 31 | 9 | | | 0.699 | 58 | 0.30 |
| 8H3 | 16 | 0.45 | 3.2 | | 0.843 | 29 | 0.53 |
| 42F2 | 22 | 8 | | | 0.754 | 40 | 0.37 |
| 25B-1 | 22.63 | 7.9 | 6.23 | | | | 0.35 |
| 7A10 | 21.8 | 7.7 | | | 0.731 | 40 | 0.35 |
| 102D5 | 9 | 8 | | | 0.791 | 21 | 0.81 |
| 11E9 | 24.85 | 7.2 | 5.25 | | 0.561 | 57 | 0.29 |
| 101 E4 | 16.0 | 7 | 3 | 0 | 0.850 | 27 | 0.44 |
| 18C7 | 28 | 7 | | | 0.737 | 48 | 0.25 |
| 25B-1 | 18.9 | 6.7 | | | | | 0.36 |
| 15E 6 | 13.05 | 6.2 | 3.8 | | 0.391 | 49 | 0.48 |
| 263H12 | 13.8 | 6 | 4 | 0 | 0.832 | 23 | 0.40 |
| 40D2 | 32 | 5 | | | 0.866 | 42 | 0.14 |
| 25B-1 | 13.53 | 4.27 | | | | | 0.32 |
| 10A4 | 28.1 | 4.2 | | | 0.190 | 170 | 0.15 |
| 6B2 | 8.55 | 4.1 | 2.9 | | 0.535 | 24 | 0.48 |
| 41G6 | 14 | 4 | | | 0.798 | 23 | 0.29 |
| 6C1 | 14.7 | 4.1 | | | 0.726 | 26 | 0.28 |
| 6A4 | 25.7 | 4.0 | | | 0.685 | 43 | 0.16 |
| 7G3 | 17.2 | 3.8 | | | 0.210 | 100 | 0.22 |
| 17G10 | 43.0 | 3.7 | | | 0.341 | 137 | 0.09 |
| 7C5 | 15.1 | 3.6 | | | 0.836 | 22 | 0.24 |
| 11E 1 | 9.55 | 3.5 | 1.6 | | 0.873 | 15 | 0.37 |
| 97D11 | 12.4 | 3 | 4 | 0 | 0.685 | 23 | 0.26 |
| 16F9 | 7 | 3 | | | 0.833 | 12 | 0.45 |
| 40G6 | 11 | 3 | | | 0.243 | 57 | 0.27 |
| 19H12 | 5 | 3 | | | 0.703 | 11 | 0.59 |
| 6F4 | 8.0 | 2.8 | | | 0.655 | 16 | 0.35 |
| 024 E5 | 14.5 | 2.5 | 3.4 | 0 | 0.697 | 24 | 0.17 |
| 52A3 | 17 | 2 | | | 0.188 | 102 | 0.13 |
| 6H4 | 6.2 | 1.2 | | | 0.307 | 24 | 0.19 |
| 37B28 | 8 | 1 | | | 0.749 | 12 | 0.15 |
| 5H8 | 8.2 | 1.2 | | | 0.725 | 13 | 0.14 |
| 97C3 | 4.9 | 1 | 2 | 0 | 0.740 | 8 | 0.20 |
| 9D7 | 19.07 | 0.00 | | | 0.626 | 30 | 0.00 |
| 7C11 | 5.3 | 0 | 0 | | 0.709 | 7 | 0.00 |
| 18H8 | 10 | 0 | 3.1 | | 0.760 | 13 | 0.00 |
| 11B3 | 2.75 | 0 | 0 | | 0.351 | 8 | 0.00 |
| 7H10 | 6.4 | 0.0 | | | 0.205 | 31 | 0.00 |
| 7B5 | 5.8 | 0.0 | | | 0.286 | 20 | 0.00 |
| 6F1 | 2.6 | 0.0 | | | 0.719 | 4 | 0.00 |
| 6B12 | 4.4 | 0.0 | | | 0.467 | 9 | 0.00 |
| 4C4 | 8.8 | 0.0 | | | 0.744 | 12 | 0.00 |
| 3H7 | 4.2 | 0.0 | | | 0.777 | 5 | 0.00 |
| 3H6 | 4.7 | 0.0 | | | 0.727 | 6 | 0.00 |
| 3G5 | 7.1 | 0.0 | | | 0.636 | 11 | 0.00 |
| 3C12 | 3.1 | 0.0 | | | 0.711 | 4 | 0.00 |
| 13G11 | 5.4 | 0.0 | | | 0.887 | 6 | 0.00 |
| 50G10 | 9 | 0 | | | 0.526 | 18 | 0.00 |
| 50F2 | 12 | 0 | | | 0.651 | 18 | |
| 48F3 | 11 | 0 | | | 0.585 | 19 | |
| 47C3 | 2 | 0 | | | 0.123 | 13 | |
| 46H5 | 8 | 0 | | | 0.375 | 20 | |
| 38 E5 | 5 | 0 | | | 0.803 | 6 | |
| 12A3 | 6 | 0 | | | 0.658 | 10 | |
| 37B11 | 2.2 | 0 | 0 | 0 | 0.158 | 14 | |
| 215B1 | 2.2 | 0 | 0 | 0 | 0.500 | 4 | |
| 25B-1 | 8.4 | 0 | 3.1 | | | | |
| 25B-1 | 7.6 | 0 | 3.1 | | | | |
| 269A7 | 4.6 | 0 | 0 | 0 | 0.08 | 58 | |

TABLE 3-continued

Strains Selected for Production of Pseudomycins and/or Growth on Minimal Medium

| Strain | PSEUDOMYCIN (μg/mL) A | B | C | C' | Cell Density ($OD_{600}$) | PSA + PSB/ $OD_{600}$ | PSB/ PSA |
|---|---|---|---|---|---|---|---|
| 7G3 | 0 | 0 | 0 | | 0.729 | 0 | |
| 17C1 | 0 | 0 | 0 | | 0.171 | 0 | |
| 13B10 | 0 | 0 | 0 | | 0.103 | 0 | |
| 10C4 | 0 | 0 | 0 | | 0.682 | 0 | |
| 9B6 | 0.0 | 0.0 | | | 0.338 | 0 | |
| 7A9 | 0.0 | 0.0 | | | 0.509 | 0 | |
| 52H7 | 0 | 0 | | | 0.828 | 0 | |
| 41A6 | 0 | 0 | | | 0.583 | 0 | |
| 16 E5 | 0 | 0 | | | 0.224 | 0 | |
| 277H4 | 0.0 | 0 | 0 | 0 | 0.123 | 0 | |

Conclusion

The selection methods and criteria disclosed herein are effective for producing strains of *P. syringae* that grow on minimal medium and produce elevated levels of one or more pseudomycins. Certain strains and conditions were identified that alter the distribution of pseudomycins produced. The lower solids and increased clarity of the minimal medium provides faster filtration of the medium and more accurate determination of cell density.

Example 3

Attempted Scale Up of Pseudomycin Production Employing Known Culture Conditions Pseudomycin Production by Static or Shaken Culture in Flasks As a first step toward large scale production of pseudomycins it was necessary to reproduce known laboratory scale methods for growing *P. syringae* and producing pseudomycins.

Materials and Methods

*P. syringae* strain MSU 16H was cultured without agitation (static or still culture) and in shaken flasks in 250 mL culture flasks for 1-10 days at 25° C. using the nutrient solution described in Table 4. This solution is similar to that used by Harrison et al. J. Gen. Microbiol. supra. As a control, *P. syringae* inoculum was added to flasks containing the nutrients of Table 4, but lacking the potato dextrose broth. In an additional test of potato derived nutrients, potato dextrose broth was replaced with a glucose (20 g/L) and potato protein (Alburex) (4 g/L) medium or a glucose (20 g/L) and potato dextrin (Avebe) (20 g/L) medium. Antifungal activity was measured as described in Example 1.

TABLE 4

Potato Dextrose Broth Plus Additives Medium (PDB Medium)

| Component | Concentration |
|---|---|
| Difco Potato Dextrose Broth | 24 g/L |
| Soluble Starch | 5 g/L |
| Glycine | 1 g/L |
| Czapek Mineral Salts Solution Stock (see Table 5) | 2 mL/L |
| MES buffer | 9.8 g/L |
| Adjust pH to 5.0 | |

TABLE 5

Czapek Mineral Salts Stock Solution

| Component | Amount |
|---|---|
| Part A | |
| KCl | 100 g |
| $MgSO_4 \cdot 7H_2O$ | 100 g |
| Deionized $H_2O$ | 900 mL |
| Part B | |
| $FeSO_4 \cdot 7H_2O$ | 2 g |
| HCl (1 N) | 2 mL |
| Deionized $H_2O$ | 98 mL |
| Add Part B to Part A slowly; mix until solution clears | |

Results

Antifungal activity was produced at levels indicative of about 10.5-29 μg/mL of pseudomycin when *P. syringae* were grown in the potato dextrose broth medium of Table 4. Static flask cultures also produced antifungal activity indicative of pseudomycin content of about 30 μg/mL under these conditions when the potato dextrose broth was replaced with a glucose and potato protein (Alburex) medium or a glucose and potato dextrin (Avebe) medium. No antifungal activity was observed in static flasks cultured under these conditions and with this nutrient solution lacking the potato products.

For incubations with the potato dextrose broth (PDB) medium, time courses of pseudomycin production demonstrated that pseudomycins were produced both in static (Table 6) flasks and in flasks shaken at 250 rpm (Table 7). Shaken flasks produced pseudomycins early in the incubation period but the pseudomycin factors disappeared after the culture pH rose to a value of 7.5 or greater. At the point of maximum total pseudomycin production in static culture, the distribution of pseudomycins was 77% A, 11% B, and 12% C. At the point of maximum total pseudomycin production in shaken culture, the distribution of pseudomycins was 67% A, 24% B, and 9% C.

TABLE 6

Time Course of Pseudomycin Production in Static Flasks Containing PDB Medium

| Incubation Period (Hours) | pH of Culture | Pseudomycins A + B + C (μg/mL) |
|---|---|---|
| 0 | 5.1 | 0 |
| 8 | 5.9 | 0 |
| 24 | 5.5 | 0 |
| 48 | 5.5 | 4 |
| 72 | 5.6 | 7 |
| 96 | 5.7 | 14.5 |
| 120 | 5.5 | 19.5 |
| 168 | 4.9 | 21.5 |
| 192 | 4.6 | 23 |
| 312 | 4.9 | 29 |

TABLE 7

Time Course of Pseudomycin Production in Shaken Flasks Containing PDB Medium

| Incubation Period (Hours) | pH of Culture | Pseudomycins A + B + C (μg/mL) |
|---|---|---|
| 0 | 5.1 | 0 |
| 8 | 5.3 | 0 |

TABLE 7-continued

| Time Course of Pseudomycin Production in Shaken Flasks Containing PDB Medium | | |
|---|---|---|
| Incubation Period (Hours) | pH of Culture | Pseudomycins A + B + C (μg/mL) |
| 24 | 5.0 | 4.5 |
| 32 | 4.6 | 9.0 |
| 40 | 4.9 | 10.5 |
| 48 | 7.5 | 6.5 |
| 56 | 7.9 | 0.5 |
| 72 | 8.3 | 0.5 |
| 80 | 8.3 | 0.5 |

For incubations with the potato dextrin medium, time courses of pseudomycin production demonstrated that pseudomycins were produced both in static flasks and in flasks shaken at 250 rpm (Table 8). The pH was adjusted to 5.0 and strain MSU 16H was inoculated into 50 mL portions of sterilized medium to start growth. In shaken flasks using this medium, some of the pH values remained below pH 6.0 and only a small loss of pseudomycins was noted. At the point of maximum total pseudomycin production in static culture, the distribution of pseudomycins was 70% A, 16% B, and 14% C. At the point of maximum total pseudomycin production in shaken culture, the distribution of pseudomycins was 62% A, 19% B, and 19% C.

TABLE 8

| Time Course of Pseudomycin Production in Shaken Flasks Containing Potato Dextrin Medium | | |
|---|---|---|
| Incubation Period (Hours) | Pseudo. in Static Flasks (A + B + C in μg/mL) | Pseudo. in Shaken Flasks (A + B + C in μg/mL) |
| 0 | 0 | 0 |
| 8 | 0 | 0 |
| 24 | 11 | 13.5 |
| 48 | 22.5 | 15.5 |
| 72 | 28.5 | 11 |
| 96 | 28.5 | 10 |

Conclusions

The known laboratory scale methods were used to produce pseudomycins. Potato products are essential for reproducing the known production method. A medium including potato protein or potato dextrin can substitute for potato dextrose broth.

Pseudomycin Production by Static or Stirred Culture in Fermentor Tanks

As a second step toward large scale production of pseudomycins, known laboratory scale methods for growing *P. syringae* and producing pseudomycins were attempted in 150 L tanks.

Materials and Methods

*P. syringae* strain MSU 16H was cultured with or without agitation in a 150 L fermentor for up to 10 days at 25° C. using the nutrient solution described in Table 4 adjusted to pH 5.2. Agitation of the 150 L tank included stirring at 75-150 rpm and sparging with air flow rates of 0.5 SCFM. In a test of alternate potato-derived nutrients, potato dextrose broth was replaced with a glucose and potato protein (Alburex) medium or a glucose and potato dextrin (Avebe) medium. Antifungal activity was measured as described in Example 1.

Results

Tank culture without agitation produced very little growth of *P. syringae* and undetectable levels of antifungal activity or pseudomycin. Agitation of the 150 L tank by stirring at low speeds and sparging with low air flow rates under these conditions also produced very little growth of *P. syringae* and undetectable levels of antifungal activity or pseudomycin. Substitution of a glucose and potato protein (Alburex) medium or a glucose and potato dextrin (Avebe) medium for the potato dextrose broth also resulted in little growth of *P. syringae* and undetectable levels of antifungal activity or pseudomycin.

Conclusion

Known methods of static culture for producing pseudomycins using *P. syringae* did not work when conducted at a 150 L scale.

Example 4

Successful Scale Up of Pseudomycin Production Employing Modified Known Culture Conditions and Media Alterations of known culture conditions for *P. syringae* were tested for their effect on pseudomycin production.

Controlling Oxygen Concentration

Materials and Methods

*P. syringae* were grown in 150 L tanks employing the conditions described in Example 3 with the potato dextrose broth (PDB) medium and control of oxygen concentration. In another test of alternative potato products, the potato pearl medium (PPM) of Table 9 was substituted for the medium of Table 4 and oxygen concentration was controlled. The potato pearls were Classic Country Style Potato Pearls® from Basic American Foods.

Dissolved oxygen concentration was controlled at 30% for the first 24 hours of culture and then, in certain runs decreased to 5% for the remaining 72 hours of the run. Dissolved oxygen was maintained at 5% by reducing the sparge rate or by blending nitrogen gas with the air sparged into the tank. These conditions were evaluated for growth of strains MSU16H and the mutant strain 25-B1. Antifungal activity was measured and pseudomycin A levels were determined as described in Example 1.

TABLE 9

| Potato Pearl Medium (PPM) | |
|---|---|
| Component | Amount |
| Glucose | 20 g/L |
| Potato Pearls | 30 g/L |
| Soluble Starch | 5 g/L |
| Glycine | 1 g/L |
| Czapek Mineral Salts Solution | 2 mL/L |
| Adjust pH to 5.2 | |

For determining a time course of pseudomycin production with a modified potato pearl medium, a 150 liter fermentor was charged with dextrose (2.3 kg), soluble starch (575 g), Basic American Foods Country Style Potato Pearls instant mashed potatoes (3.45 kg), glycine (115 g), $MgSO_4.7H_2O$ (23 g), KCl (23 g), $FeSO_4.7H_2O$ (0.46 g), and 115 L of water. The pH was adjusted to 5.0. Seed culture of strain 25-B1 (1.8 liters) was inoculated into the fermentor following steam sterilization and cooling. Fermentor agitation was set at 150 rpm and air flow was set at 0.5 SCFM (0.14 vvm.). Agitation and air flow were adjusted automatically during the run to maintain dissolved oxygen at 30% of saturation. The temperature was controlled at 25° C. The culture pH was kept at or below 5.5 through the addition of 30% $H_2SO_4$.

For an even larger scale run, a 1000 liter fermentor was charged with Difco PDB (24.0 kg), soluble starch (5.0 kg), glycine (1.0 kg), $MgSO_4.7H_2O$ (200 g), KCl (200 g), $FeSO_4.7H_2O$ (4 g), and 1000 liters of water. The pH was adjusted to 5.0. Fifty liters of a 16-hour seed culture of strain MSU 16H were inoculated into the fermentor. The temperature was controlled at 25° C. and the dissolved oxygen was maintained at or above 30% of saturation with agitation and sparged air. The pH was controlled so as not to exceed a value of 5.5 through the addition of 30% $H_2SO_4$.

Results

Antifungal activity was produced by culturing in a 150 L tank when the oxygen concentration was controlled (Table 10). Control of oxygen levels by addition of nitrogen gas to the sparge resulted in higher levels of pseudomycin. Substitution of mutant *P. syringae* strain 25-B1 for strain MSU 16H approximately doubled both growth of the microbe and yield of antifungal activity (Table 10). A further approximate doubling of growth and yield was obtained by substituting the nutrient medium of Table 9 for the medium of Table 4.

TABLE 10

Production of Pseudomycins With Two Potato Media and Control of Oxygen Level

| Strain | Total Titer and Pseudomycin A[1] in μg/mL PDB with nitrogen sparge | PDB lacking nitrogen sparge | PPM with nitrogen sparge | PPM lacking nitrogen sparge |
|---|---|---|---|---|
| MSU 16H | 21 (8) | 12 (ND)[2] | NT[3] | NT |
| 25-B1 | 49 (27) | 20 (13) | 87 (37) | 75 (44) |

[1]Pseudomycin A titers are shown in parentheses
[2]ND denotes not determined
[3]NT denotes not tested The time course of pseudomycin production is shown in Table 11. In this time course at 150 L, the distribution of pseudomycin factors produced by this fermentation was 79% A, 10% B, and 11% C. Factor C' was produced in trace amounts.

TABLE 11

Time Course of Pseudomycin Production in 150 L Fermentor Containing Potato Pearl Medium

| Elapsed Fermentation Time (Hours) | Pseudomycins A + B + C (μg/mL) |
|---|---|
| 0 | 0 |
| 8 | 0 |
| 16 | 17 |
| 24 | 35 |
| 32 | 45 |
| 40 | 41 |

In the 1000 L fermentor run a similar time course for production of pseudomycins was obtained (Table 12).

TABLE 12

Time course of Pseudomycin Production in 1000 L Fermentor Containing a Modified Potato Dextrose Medium

| Elapsed Fermentation Time (Hours) | Pseudomycins A + B + C (μg/mL) |
|---|---|
| 0 | 0 |
| 4 | 0 |
| 16 | 5.2 |
| 28 | 5.6 |
| 40 | 5.9 |
| 52 | 5.8 |
| 76 | 6.0 |
| 100 | 6.3 |

Conclusions

Yield of pseudomycins can be significantly increased by control of factors such as dissolved oxygen concentration, strain selection, and further changes in medium composition.

Supplementation with Lipid and Additional Ingredients

The potato pearl medium of Table 9 was supplemented with additional ingredients to determine their effect on pseudomycin production.

Materials and Methods

The potato pearl medium of Table 9 was supplemented with additional ingredients such as lipid (e.g., methyl myristate or soybean oil), phosphate, higher concentrations of glycine, ammonium hydroxide feeding, and glucose feeding (Table 13). Cell growth was conducted as described above. Antifungal activity was measured as described in Example 1.

Results

The results of these experiments are shown below in Table 13.

TABLE 13

Increased Yield of Pseudomycin with Supplementation of the Potato Pearl Medium.

| Supplement | Yield of Pseudomycin A + B + C (μg/mL) |
|---|---|
| none | 80 |
| methyl myristate (1 g/L) | 150 |
| glycine (2 g/L) | 110 |
| feed ammonium hydroxide (10 mL/hr) | 110 |
| glycine at 2 g/L and methyl myristate (1 g/L) | 160 |
| glycine (4 g/L) | 240 |
| glucose feed (200 mL/hr) | 80 |
| glycine (4 g/L), methyl myristate at 1 g/L, and glucose feed | 287 |
| soybean oil (1 g/L) | 150 |
| $KH_2PO_4$ (0.5 g/L) | 60 |

Conclusions

Supplementation of the medium with glycine and methyl myristate significantly increases production of pseudomycins by *P. syringae*. Glucose feeding is also advantageous.

Example 5

Glycine and Methyl Myristate Stimulate Production of Pseudomycins

The effects of glycine, methyl myristate and several other components on production of pseudomycins were determined to allow production of improved levels of pseudomycins.

Materials and Methods

*P. syringae* were grown in 50 mL of culture medium in a 250 mL flask. The culture was started with an inoculum of *P. syringae* MSU 16H and maintained at 25° C. and 70% humidity for 7 days without shaking in an incubator. At the end of the incubation period, 4 mL of the broth are removed from the flask and mixed with 6 mL of methanol containing 0.1% phosphoric acid. It is believed that low pH stabilizes the pseudomycins. Particulate matter is removed by filtration or centrifugation and the pseudomycins are determined by HPLC as described in Example 1.

The media used in this study are potato dextrose broth (PDB, Difco) at 24 g/L in water sterilized (control medium); the control medium plus 2 mL/L Czapek mineral salts solution; control medium plus 1 g/L glycine; control medium plus 1 mL/L methyl myristate (Sigma); control medium plus 5 g/L soluble starch (Difco); control medium plus 2 mL/L Czapek mineral salts solution, 1 g/L glycine, and 5 g/L soluble starch; and control medium plus 2 mL/L Czapek mineral salts solution, 1 g/L glycine, 1 mL/L methyl myristate, and 5 g/L soluble starch.

On the same day the same media were used to grow *P. syringae* in shaken flasks for 30 hours at the conditions described above except with shaking. The flasks were shaken at 250 rpm.

In another experiment with shaken flasks, control medium was compared to control media including glycine and several other additives. The cells were grown as described above for shaken flasks. The media employed were control medium; control medium plus 1 g/L glycine; control medium plus 1 g/L glycine and 2 mL/L Czapek mineral salts solution; control medium plus 1 g/L glycine and 5 g/L soluble starch; control medium plus 1 g/L glycine and 1 mL/L methyl myristate; control medium plus 1 g/L glycine, 2 mL/L Czapek mineral salts solution, and 5 g/L soluble starch; and control medium plus 1 g/L glycine, 2 mL/L Czapek mineral salts solution, 1 mL/L methyl myristate, and 5 g/L soluble starch.

Results

Figure 3:
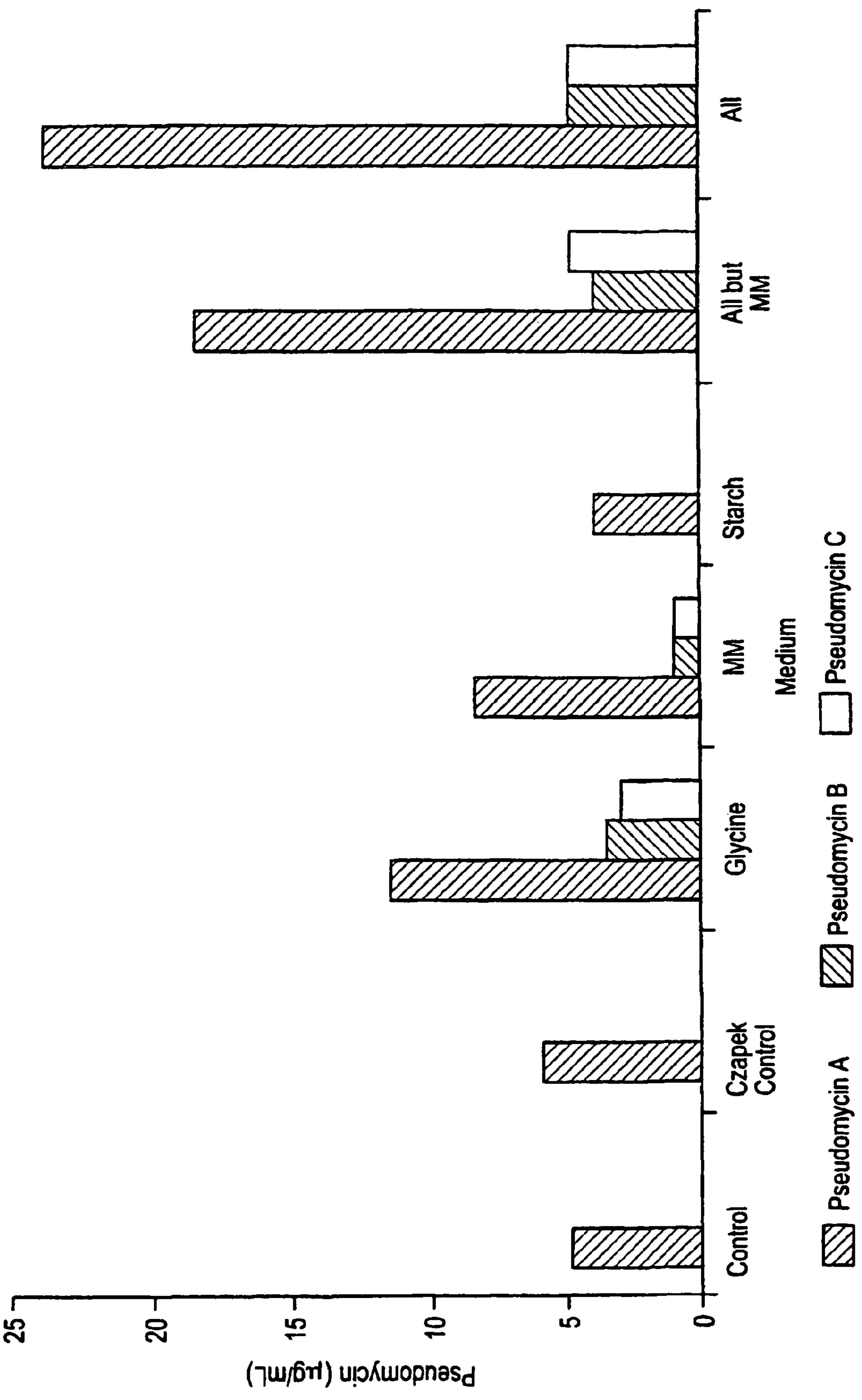
FIG. 3 illustrates production of pseudomycins A, B, and/or C employing *P. syringae* strain MSU 16H in unshaken flasks with a medium including potato dextrose broth and in that medium plus salts, glycine, methyl myristate, and/or soluble starch.

The results obtained with unshaken flasks are shown in FIG. 3. The control medium is that used by G. Strobel et al. of Montana State for growing *P. syringae* as described in Harrison et al. J. Gen. Microbiol. supra. The detection limit for pseudomycins in this experiment is about 1 μg/mL. FIG. 3 illustrates that the known medium and conditions taken from the work of G. Strobel produce about 5 μg/mL of pseudomycin A and undetectable levels of pseudomycins B and C. Addition of Czapek mineral salts solution to the control medium results in a slight increase in pseudomycin A production, to about 6.5 μg/mL, and undetectable levels of pseudomycins B and C. Addition of 1 g/L glycine to the control medium results in a significant increase in pseudomycin A production to about 10.5 μg/mL and detectable production of pseudomycin B (2.5 μg/mL), but undetectable levels of pseudomycin C. Addition of methyl myristate to the control medium results in a significant increase pseudomycin A production to 8 μg/mL, and detectable production of about 1 μg/mL of each of pseudomycins B and C. Addition of soluble starch to the control medium results in a slight depression of production of pseudomycin A and undetectable levels of pseudomycins B and C. A dramatic and greater than additive increase in production of pseudomycins A, B and C is observed using control medium plus the Czapek mineral salts solution, glycine, and soluble starch (FIG. 3). A further increase is seen when methyl myristate is added to the control medium plus Czapek mineral salts solution, glycine, and soluble starch (FIG. 3). For the unshaken flasks, each result is a mean of 3 flask cultures.

Figure 4:
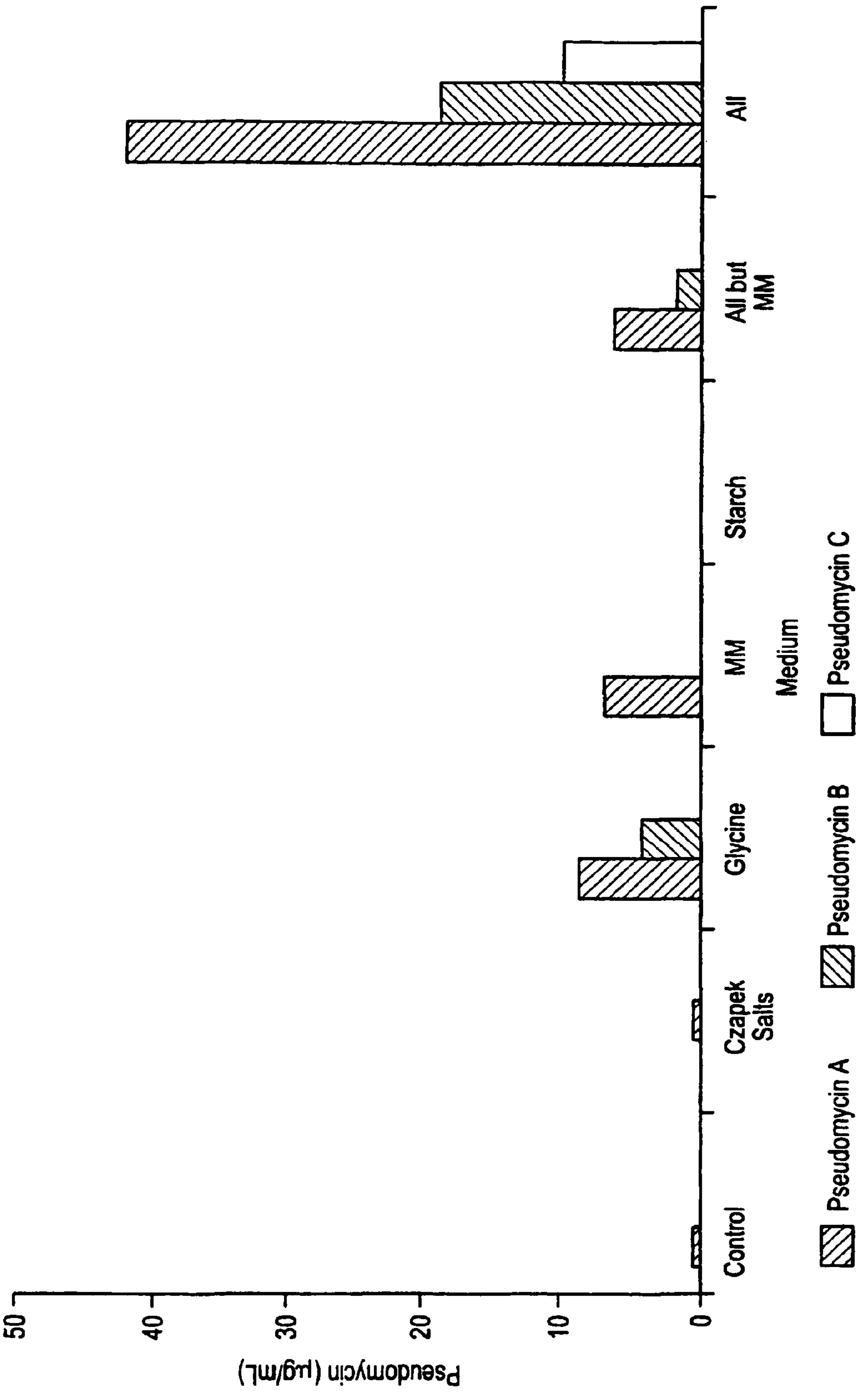
FIG. 4 illustrates pseudomycin production under the conditions described for FIG. 3, except the flasks are shaken.
Figure 5:
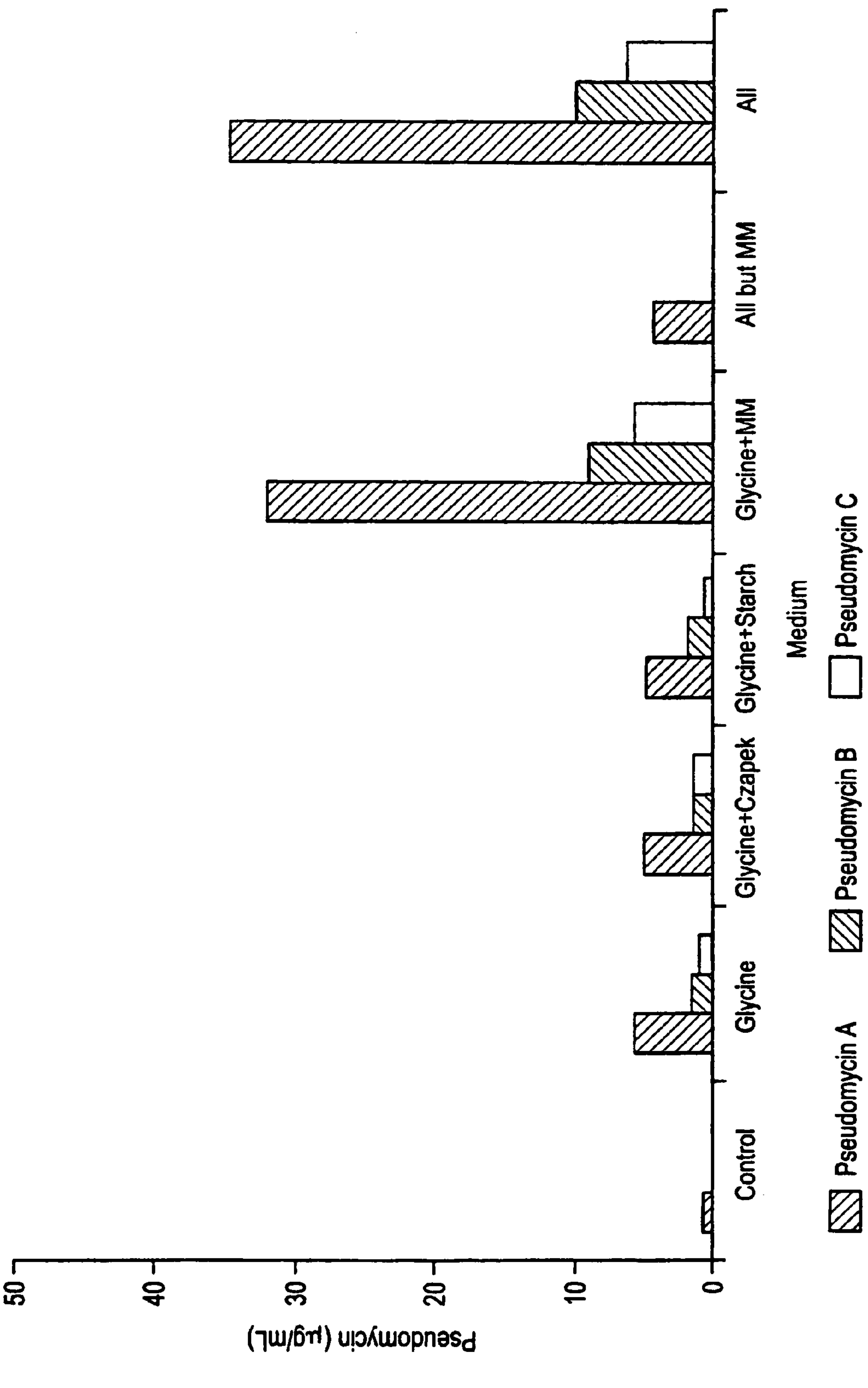
FIG. 5 illustrates production of pseudomycins employing glycine containing media and shaken flasks as described for FIG. 4. These results illustrate synergy between glycine and methyl myristate in stimulating pseudomycin production.

As shown in FIG. 4, similar results are obtained in shaken flasks. However, in the shaken flasks, addition of glycine or methyl myristate is essential to obtaining more than minimal levels of pseudomycin A and the combination of glycine and methyl myristate causes a dramatic and more than additive increase in levels of each of pseudomycins A, B and C. Similar results are observed with the combinations and ingredients shown in FIG. 6.

Conclusions

In unshaken flasks, glycine and/or methyl myristate each cause significant increases in production of pseudomycins A and B. Methyl myristate stimulates production of pseudomycin C. In shaken flasks, the presence of glycine or methyl myristate is required for significant production of pseudomycin A. Furthermore, glycine and methyl myristate exhibit synergy in stimulation of production of pseudomycins A, B and C.

Example 6

Among Fatty Acid Methyl Esters, Methyl Myristate and Methyl Palmitate Stimulate Production of Pseudomycins

*P. syringae* were cultured in the presence of fatty acid methyl esters of different chain lengths to demonstrate that stimulation of pseudomycin production depends on the carbon chain length.

Materials and Methods

*P. syringae* were cultured as described in Example 5 with shaking in a medium including methyl esters of the fatty acids at a concentration of 0.1% v/v in control potato dextrose broth medium plus 1 g/L glycine, 2 mL/L Czapek mineral salts solution, 5 g/L soluble starch, at pH 5.0. Pseudomycins were determined by HPLC as described in Example 1.

Results

Figure 6:
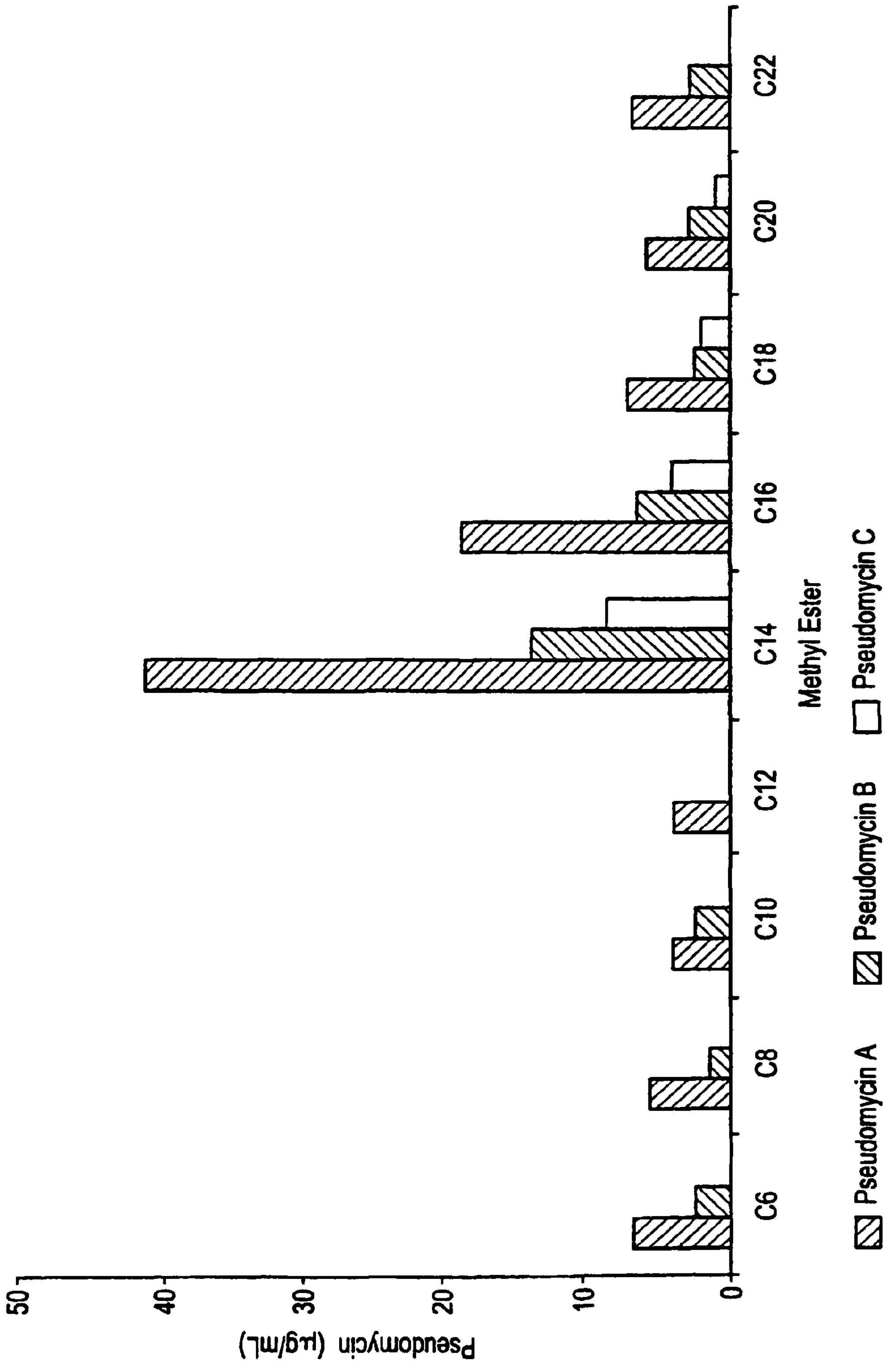
FIG. 6 illustrates production of pseudomycin A, B, and/or C by *P. syringae* strain MSU 16H in the presence of various fatty acid methyl esters added at a concentration of 0.1% v/v to medium including potato dextrose broth, glycine, salts, and soluble starch. Each of the fatty acids was saturated and the numbers under the bars represent the length of the carbon chain.
Figure 7:
FIG. 7 illustrates pseudomycin factor titers in a 150 liter fermentation. Dissolved oxygen was controlled at 30% by computer-controlled adjustment of agitation and air flow. Glucose was fed at 200 mL/h beginning at 18 h and ammonium hydroxide was fed at 20 mL/h beginning at 20 h. No pseudomycin C' was detected in this fermentation.

FIG. 6 shows the results obtained from incubations of *P. syringae* with fatty acid methyl esters having even numbered carbon chain lengths from 6 to 22 carbon atoms. Levels of pseudomycins similar to those obtained in Example 5 for incubations without methyl myristate were produced by fatty acid methyl esters having 6 to 12 or 18 to 22 carbon atoms in their chains (FIG. 6). A significant increase in pseudomycin production was seen with 14 and 16 carbon chains. Methyl myristate is the 14 carbon fatty acid methyl ester. Each of the 14 and 16 carbon chain fatty acids methyl esters significantly increased production of each of pseudomycins A, B and C.

Conclusions

Among the fatty acid methyl esters tested, methyl myristate produces the largest amounts of pseudomycins employing strain MSU 16H. Significantly, the fatty chain attached to the peptide ring of pseudomycins is a 14 carbon chain. This suggests that the added methyl myristate may serve as a precursor to the pseudomycins.

Example 7

Procedures for Tank-Scale Production of Pseudomycins with a Medium Including Potato Product Medium developed according to Examples 4 and 5 can be used for production of pseudomycins by growing *P. syringae* on a 150 L and 5000 L scale in medium containing potato product.

Production Employing a 150 L Tank Fermentor

Materials and Methods:

Vegetative-stage flasks containing complete streptomyces medium (CSM, Table 2) were inoculated with a frozen *P. syringae* culture and were shaken at 250 rpm and 25° C. for 24 hours. After 24 hours of incubation of the vegetative-stage flasks, the contents of these flasks was used to inoculate bump-stage flasks. The bump-stage flasks include the CSM medium and were rotated at 250 rpm and held at 25° C. The bump-stage flasks were inoculated with about 0.45 mL of pooled culture from three or four vegetative-stage flasks. The bump stage flasks typically include about 900 mL of CSM in a non-baffled 2.5 L Tunair™ flask. Two bump-stage cultures in Tunair™ flasks were set for each fermentor. The bump-stage flasks were incubated for 16 hours.

Then, two of the bump-stage cultures (1.8 L total volume) were pooled by combining in an inoculation bazooka. These combined cultures were used to inoculate 115 L of the medium described in Table 9 that has been supplemented with an additional 3 g/L (for a total of 4 g/L) of glycine and 1 g/L of soybean oil. These large-scale cultures were grown at 25° C. for three to four days. During this growing period, dissolved oxygen was controlled at 30% of air saturation with agitation and air flow. pH was controlled at 5.2±0.2 by addition of sulfuric acid or sodium hydroxide as required. Eighteen hours after beginning the large-scale culture, a glucose feed was started at a rate of 200 mL/h. Twenty hours after the start of the large-scale culture, ammonium hydroxide feed was started at a rate of 20 mL/h. During this culture, the holdback pressure was 5 psig. The initial setting for agitation was 150 rpm and air flow is 0.5 scfm. If required, an anti-foam agent was added, as well. After the three to four days of large-scale culture, the *P. syringae* were harvested. Antifungal activity was measured as described in Example 1.

Results

Figure 8:
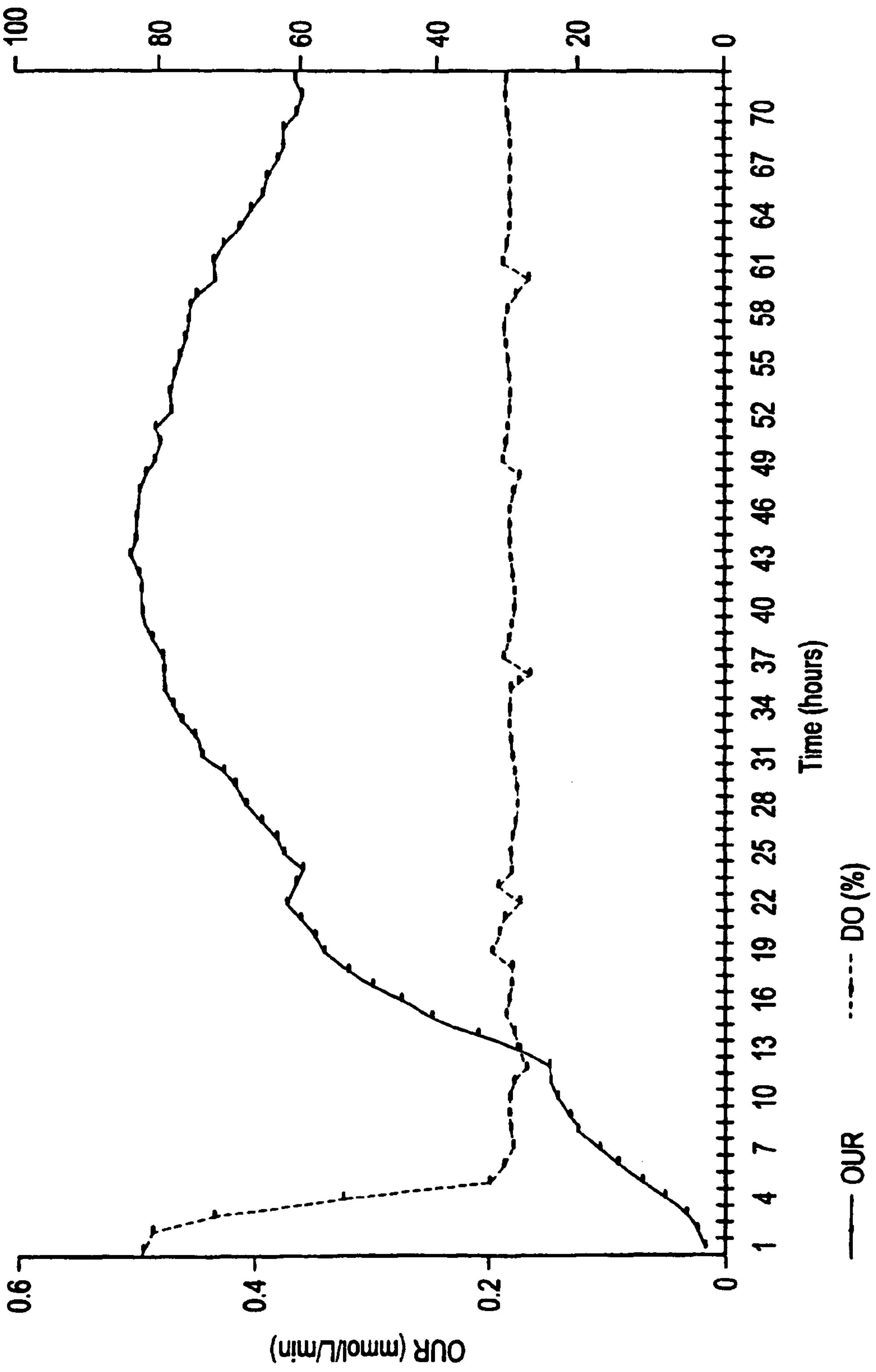
FIG. 8 illustrates oxygen uptake and dissolved oxygen in the 150 liter fermentation run for which pseudomycin production is illustrated in FIG. 7.
Figure 9:
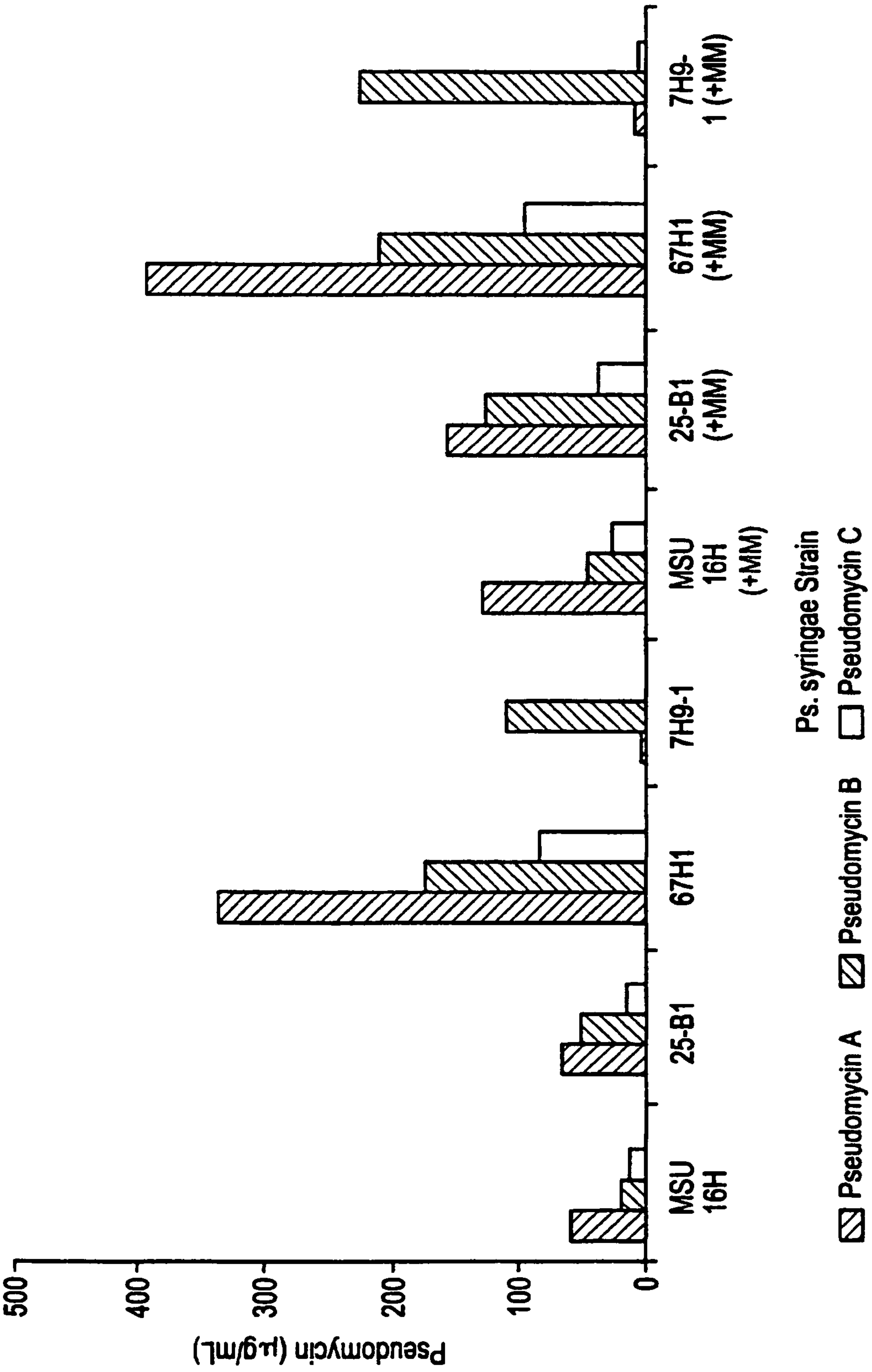
FIG. 9 illustrates production of pseudomycins A, B, and/or C by various strains of *P. syringae* employing a medium free of added potato products and with or without methyl myristate in shaken flasks.

Profiles for several different fermentation parameters in a run conducted by this procedure are shown in FIGS. 8 and 9.

Conclusions

Significant and commercially viable amounts of pseudomycins can be produced using this method.

Production Employing a 5000 L Tank Fermentor

The methods developed for successful production of pseudomycins at a 150 L scale were scaled up further to 5000 L.

Materials and Methods

Inoculant *P. syringae* were prepared as described above for the 150 L scale fermentor. Conditions were as described above for the 150 L scale with modifications as described in Table 14. Four trials were run, the first three of which were satellited by aseptic transfer of inoculated broth to a sterile 150 liter tank. The satellites served to eliminate nutrient make-up and sterilization as variables when comparing performance in the 150 L and 5000 L fermentors. Antifungal activity was measured as described in Example 1.

Results

Table 14 summarizes the results obtained at the 5000 liter scale and how they compared to the satellite runs. Titers in the 5000 L tank essentially matched those in the 150 L tank except in Trial 1. In Trial 1, the agitation in the 5000 L tank was initially set at 150 rpm and then reduced to 50 rpm at 36 hours. The level of cell growth was only one-third that of the 150 L tank satellite and the pseudomycin A titer was one-fourth that of the satellite. Reducing the 5000 L tank agitation to 25 rpm (initial setting) in subsequent trials resulted in levels of cell growth and pseudomycin titers comparable to satellites and individually run 150 L tanks. The data suggest that *P. syringae* strain 25-B1 is sensitive to shear.

TABLE 14

Results of Scale-Up to 5000 Liter Fermentors (PPM)

| Trial | 5000 L Lot | Titer[1] | Satellite Lot | Titer | Comments |
|---|---|---|---|---|---|
| 1 | 055CE7 | 12 | 313CA7 | 45 | 4 g/L glycine, 0.1 g/L methyl myristate, no pH control, no feeds; in the 5000 L tank: $DO_2$ high, reduce agitation from 150 to 50 rpm at 36 h |
| 2 | 060CE7 | 89 | 318CA7 | 77 | Same as trial 1 but medium included 1 g/L methyl myristate; in the 5000 L tank: agitation at 25 rpm, $DO_2$ controlled at 30% |
| 3 | 063CE7 | 50 | 332CA7 | 44 | Medium as per trial 1 but including Potato Pearls at 10 g/L and caramelized broth. After a rapid drop in pH, raise to 5.5 at 24 h with $NH_4OH$ |
| 4 | 068CE7 | 120 | Not Done | 135 | pH controlled @ 5.2 with NaOH and ammonium hydroxide feed, also glucose feed, medium as per trial 1 except with soybean oil in medium rather than methyl myristate |

[1]Titer denotes pseudomycin A in μg/mL.

Glucose feeding of fermentors used an 80% w/v solution of glucose and ammonia feeding used a 58% w/w solution of ammonium hydroxide.

Conclusions

Significant and commercially viable levels of pseudomycins can be produced employing this method at a 5000 liter scale.

Example 8

Lane Scale Growth of *P. syringae* and Production of Pseudomycins in Medium Lackine Potato Products Fermentation of *P. syringae* in medium N21, which does not include any of the potato products used in media described in the previous Examples, produced pseudomycins at levels suitable for isolation of gram amounts.

Production of Pseudomycins in Shaken Flasks and N21 Medium

Materials and Methods

*P. syringae* were cultured under conditions described in Example 5, with the exception that the medium included no potato products. This medium, known as N21 medium has the composition shown in Table 15. For determination of the effect of methyl myristate on pseudomycin production, methyl myristate was added at a concentration of 0.2%.

TABLE 15

The Composition of N21 Medium

| INGREDIENT | GRAMS PER LITER |
|---|---|
| Sucrose | 35 |
| Ammonium Sulfate | 0.5 |
| Monosodium Glutamate | 2 |
| L-Histidine | 2 |
| Glycine | 0.5 |
| Soluble Starch | 5 |
| $KH_2PO_4$ | 0.2 |
| Czapek Mineral Salts Solution | 2 mL |
| Yeast Extract | 1 |
| MES Buffer | 9.8 |
| Adjust pH to 5.2 | |

Production of pseudomycin by several strains of *P. syringae* was evaluated employing N21 medium with and without methyl myristate. The strains of *P. syringae* evaluated were MSU 16H, 25-B1, 67H1, and 7H9-1.

Results

The results of studies of production of pseudomycins by various strains of *P. syringae* with and without methyl myristate are shown in Table 16 and FIG. 9. These results show that strain 67H1 produces higher levels of each of the pseudomycins either in the presence or absence of methyl myristate. Strain 7H9-1 is distinctive for producing pseudomycin B at much higher levels that either pseudomycin A or C. Methyl myristate stimulated pseudomycin production for each of the strains.

TABLE 16

Production of Pseudomycins by Several Strains of *P. syringae* With and Without Methyl Myristate

| Strain | Methyl Myristate | Pseudomycin A μg/mL | Pseudomycin B μg/mL | Pseudomycin C μg/mL |
|---|---|---|---|---|
| MSU 16 H | – | 59 | 19 | 12 |
| 25-B1 | – | 66 | 50 | 15 |
| 67H1 | – | 334 | 173 | 83 |
| 7H9-1 | – | 3 | 110 | 0 |
| MSU 16H | + | 126 | 45 | 27 |
| 25-B1 | + | 154 | 123 | 36 |
| 67H1 | + | 390 | 207 | 95 |
| 7H9-1 | + | 8.5 | 222 | 4.5 |

Conclusions

Various strains of *P. syringae* produce commercially significant levels of pseudomycins in medium lacking potato products, and this production is stimulated by methyl myristate.

Production of Pseudomycins at a Scale of 5000 L Employing N21 Medium

The methods for producing pseudomycins employing a medium without added potato products was scaled up to a 5000 liter level.

Materials and Methods

Production of pseudomycins in a 5000 L fermentor was conducted as described in Example 7, with the exception that the medium employed was N21 medium (Table 15). The N21 medium was supplemented with yeast extract at 1 g/L. The strain employed was *P. syringae* 67H1.

Results

Mean values from ten 5000 L fermentor trials are reported in Table 17.

TABLE 17

Profile of Mean Amounts of Pseudomycins Obtained in Ten 5000 L Fermentor Runs

| Pseudomycin | μg/mL at Harvest |
|---|---|
| A | 243 |
| B | 203 |
| C | 71 |
| C' | 40 |

Conclusions

Pseudomycins A, B, C, and C' can be produced in commercially significant amounts at the 5,000 L scale employing a medium free of added potato products.

Example 9

Further Simplification of Medium for Production of Pseudomycins

Fermentation of *P. syringae* in medium N21SM resulted in successful production of pseudomycins in the absence of potato products. Media based on N21SM but lacking certain of its ingredients also support production of pseudomycins at significant levels.

Materials and Methods

*P. syringae* were cultured in shake flasks under conditions described in Example 5, with the exception that the medium is as described below. The base medium, known as CNP medium has the composition shown in Table 18. Additives were tested at the concentrations and in the combinations listed below (Table 18).

TABLE 18

The Composition of CNP Medium

| INGREDIENT | QUANTITY |
|---|---|
| Glucose | 20 g/L |
| $KH_2PO_4$ | 0.41 g/L |
| Czapek Mineral Salts Solution | 2 mL |
| MES Buffer | 9.8 g/L |
| Ammonium Sulfate | 1 g/L |
| Adjust pH to 5.2 | |
| ADDITIVES TO CNP MEDIUM | |
| Glutamate | 2 g/L |
| Glycine | 0.5 g/L |
| L-Histidine | 2 g/L |
| Soluble Starch | 5 g/L |
| Yeast Extract | 1 g/L |

Production of pseudomycin by several strains of *P. syringae* was evaluated employing CNP medium with and without one or more of the additives. The strain of *P. syringae* 25-B1 was one of the strains evaluated.

Results

The results of studies of production of pseudomycins by *P. syringae* with and without the additives are shown in Table 19.

TABLE 19

Production of Pseudomycins By *P. syringae* in CNP Medium With and Without Additives

| | | Pseudomycin (μg/mL) | | | |
|---|---|---|---|---|---|
| Additive | $OD_{600}$ | A | B | C | C' |
| None | 0.221 | 0 | 0 | 0 | 0 |
| | 0.222 | 0 | 0 | 0 | 0 |
| Glutamate | 0.943 | 82.6 | 16.3 | 24.5 | 5.9 |
| | 0.94 | 87 | 16.7 | 25.7 | 6 |
| Glycine | 0.628 | 0 | 0 | 0 | 0 |
| | 0.567 | 0 | 0 | 0 | 0 |
| Histidine | 0.331 | 0 | 0 | 0 | 0 |
| | 0.354 | 0 | 0 | 0 | 0 |
| Glutamate, Glycine, | 0.984 | 153 | 41 | 44 | 12 |
| and Histidine | 0.98 | 149 | 40 | 42 | 12 |
| Glutamate, Glycine, | 0.985 | 134 | 29 | 34 | 9 |
| Histidine, and Soluble Starch | 0.996 | 125 | 34 | 35 | 11 |
| Soluble Starch | 0.28 | 0 | 0 | 0 | 0 |
| | 0.289 | 0 | 0 | 0 | 0 |
| Yeast Extract | 0.441 | 40 | 6 | 11 | 2 |
| | 0.449 | 39 | 6 | 11 | 2 |
| Glutamate, Glycine, | 0.998 | 215 | 52 | 55 | 17 |
| Histidine, Soluble Starch, and Yeast Extract | 1.001 | 197 | 52 | 56 | 19 |

Conclusions

Various minimal media can be used for growth of *P. syringae* and production of commercially significant levels of pseudomycins.

Example 10

Production of Pseudomycins A' and B'

Fermentation methods were developed for producing pseudomycin A' and/or B' in the fermentation broth of a *Pseudomonas syringae* strain.

Materials and Methods

Preparation of inoculum: An aliquot of cells stored in the vapor phase of liquid nitrogen was thawed and used to inoculate two 900 mL portions of CSM broth. CSM broth was composed of (g/L): dextrose (5), maltose (4), Difco Tryptic Soy Broth (30), Difco yeast extract (3), and $MgSO_47H_2O$(2). Approximately 0.5 mL of cells was used to inoculate each 900 mL portion of medium contained in a two liter flask. Flasks were incubated with shaking for 24 hours at 25° C. The contents of two flasks were combined to inoculate a 150 liter fermentor containing 115 liters of sterile fermentation broth.

Fermentation Stage: Fermentation broth was composed of (g/L): dextrose (20), soluble starch (5), Basic American Foods Country Style Potato Pearls instant mashed potatoes (30), glycine (1), $MgSO_47H_2O$(0.2), KCl (0.2), and $FeSO_47H_2O$(0.004) in tap water. The pH was adjusted to 5.2 before sterilization. Fermentation was carried out at 25° C. for 68 hr. Dissolved oxygen was maintained at or above 30% of air saturation by continuous adjustment of air flow and impeller agitation rate. The pH was maintained between 4.0 and 5.4 through the addition of either $H_2SO_4$ or NaOH.

Variations on the Batch Methods: Several variations of the simple batch process were also found to produce pseudomycins A' and/or B'. Dextrose can be fed to the fermentors starting 24 hours after initial inoculation at a rate of 60 mL per hour. Feeding can be continued throughout the course of the fermentation. Alternatively, a process has been used where dissolved oxygen is maintained at 5% of air saturation starting 24 hours after inoculation and continuing until the end of the fermentation period. Maintenance of dissolved oxygen at 5% was achieved through addition of inert nitrogen gas ($N_2$) to the air supply leading to the fermentor. In all cases, gas was supplied through a single submerged sparger tube with an opening positioned just below the bottom agitator turbine in the fermentor.

Results and Conclusions

Several fermentation methods produce pseudomycin A' and/or B' from *P. syringae*.

Isolation and Purification of Pseudomycins A' and B'

Methods were developed for isolation and purification pseudomycins A' and B' from the fermentation broth of a *Pseudomonas syringae* strain.

Materials and Methods

The whole fermentation broth (4×100 L) after harvest was filtered through a Membralox ceramic filter (0.45 μm) to afford a filtrate (fraction A) and a solid slurry (fraction B). Fraction B (135 L) was extracted with an equal volume of acetone containing 0.1% TFA for 120 min and allowed to settle. The clear acetone extract was separated by filtration and then evaporated in vacuo to an aqueous solution to yield fraction C (88 L). First, fraction A was charged on to a HP20ss resin column (10 L) packed in water and the column was washed with 15% acetonitrile containing 0.1% TFA (20 L). Fraction C was then loaded on to the sarne column and the column was washed with 20 L of 15% acetonitrile containing 0.1% TFA as before.

The column was then eluted with a linear gradient of 15-20% acetonitrile containing 0.1% TFA over 30 min and 20-35% acetonitrile containing 0.1% TFA over 60 min with 1 L/min flow rate. One liter fractions were collected. Fractions 6-9 were combined (4 L) to yield fraction D (24 g). A portion of fraction D (−1 g) was chromatographed over a reversed-phase column (Dynamax $C_{18}$ 41.4×250 mm) using triethylammonium phosphate buffer (pH 3)-acetonitrile-methanol as mobile phase (65:17:18 to 30:35:35 gradient elution over 45 min with 40 ml/min flow rate). Appropriate fractions were combined, volume was reduced to 75 ml and rechromatographed over a $C_{18}$ column as before using a gradient 80:10:10 to 46:27:27 to afford fraction E (113 mg) and fraction F (116 mg). Further chromatography of fractions E and F over a $C_{18}$ column (Dynamax 21.4×250 mm) furnished 45 mg pseudomycin A' and 62 mg of pseudomycin B', respectively.

Results and Conclusions

HPLC methods similar to those used to purify other pseudomycins resulted in purification of pseudomycins A' and B' from fermentation broth.

The invention has been described with reference to various specific and preferred embodiments and techniques. However, it should be understood that many variations and modifications may be made while remaining within the spirit and scope of the invention. All publications and patent applications in this specification are indicative of the level of ordinary skill in the art to which this invention pertains.

We claim:

1. A biologically pure culture of *Pseudomonas syringae* strain 25-B1 (ATCC PTA-1622) or a pseudomycin producing mutant thereof having all of the identifying characteristics of said strain.

2. The biologically pure culture of claim 1, wherein said *Pseudomonas syringae* or said pseudomycin producing mutant thereof produces one or more pseudomycins in an amount greater than about 10 μg/mL.

3. The biologically pure culture of claim 2, wherein said biologically pure culture of *Pseudomonas syringae* or said pseudomycin producing mutant thereof produces a pseudomycin in an amount of about 200 μg/mL to about 900 μg/mL.

4. A biologically pure culture of *Pseudomonas syringae* strain 67H1 (ATCC PTA-1621) or a pseudomycin producing mutant thereof having all of the identifying characteristics of said strain.

5. The biologically pure culture of claim 4, wherein said *Pseudomonas syringae* or said pseudomycin producing mutant thereof produces one or more pseudomycins in an amount greater than about 10 μg/mL.

6. The biologically pure culture of claim 5, wherein said biologically pure culture of *Pseudomonas syringae* or said pseudomycin producing mutant thereof produces a pseudomycin in an amount of about 200 μg/mL to about 900 μg/mL.

7. A biologically pure culture of *Pseudomonas syringae* strain 7H9-1 (ATCC PTA-1623) or a pseudomycin producing mutant thereof having all of the identifying characteristics of said strain.

8. The biologically pure culture of claim 7, wherein said *Pseudomonas syringae* or said pseudomycin producing mutant thereof produces one or more pseudomycins in an amount greater than about 10 μg/mL.

9. The biologically pure culture of claim 8, wherein said biologically pure culture of *Pseudomonas syringae* or said pseudomycin producing mutant thereof produces a pseudomycin in an amount of about 200 μg/mL to about 900 μg/mL.

10. A composition comprising a biologically pure culture of *Pseudomonas syringae* selected from the group consisting of strain 25-B1 (ATCC PTA-1622), 67H1 (ATCC PTA-1621) and 7H9-1 (ATCC PTA-1623), or a pseudomycin producing mutant thereof having all of the identifying characteristics of said strain; and an aqueous nutrient medium.

11. The composition of claim 10, wherein said *Pseudomonas syringae* is strain 25-B1 (ATCC PTA-1622).

12. The composition of claim 10, wherein said *Pseudomonas syringae* is strain 67H1 (ATCC PTA-1621).

13. The composition of claim 10, wherein said *Pseudomonas syringae* is strain 7H9-1 (ATCC PTA-1623).

14. The composition of claim 10, wherein said biologically pure culture of *Pseudomonas syringae* or said pseudomycin producing mutant thereof produces a pseudomycin in an amount of about 200 μg/mL to about 900 μg/mL.

15. The composition of claim 14, wherein said biologically pure culture of *Pseudomonas syringae* or said pseudomycin producing mutant thereof produces a pseudomycin in an amount of about 600 μg/mL to about 900 μg/mL.

16. The composition of claim 15, wherein said biologically pure culture of *Pseudomonas syringae* or said pseudomycin producing mutant thereof produces a pseudomycin in an amount of about 800 μg/mL to about 900 μg/mL.

* * * * *